US006692930B2

(12) United States Patent
Hsieh

(10) Patent No.: US 6,692,930 B2
(45) Date of Patent: Feb. 17, 2004

(54) MONOCLONAL ANTIBODIES SPECIFIC TO COOKED MEATS

(75) Inventor: Y. H. Peggy Hsieh, Auburn, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 09/963,986

(22) Filed: Sep. 26, 2001

(65) Prior Publication Data

US 2002/0123070 A1 Sep. 5, 2002

Related U.S. Application Data

(63) Continuation of application No. 09/225,141, filed on Jan. 4, 1999.
(60) Provisional application No. 60/024,887, filed on Aug. 30, 1996.

(51) Int. Cl.[7] .................. G01N 33/53; G01N 33/537
(52) U.S. Cl. .................. 435/7.92; 530/387.1; 436/548; 435/7.1; 435/7.94; 435/332; 424/141.1; 424/152.1
(58) Field of Search .................. 530/387.1, 388.2; 436/548; 435/7.1, 7.94, 332, 7.92; 424/141.1, 152.1

(56) References Cited

U.S. PATENT DOCUMENTS

| 5,312,751 A | 5/1994 | Michel et al. |
| 5,338,661 A | 8/1994 | Jensenius et al. |

OTHER PUBLICATIONS

Köhler et al., Nature, 256, 495–497, 1975.*
Sevier er al., Clin. Chem. 27, 11, 1797–1806, 1981.*
Abouzied, M.M., et al. "Lactate Dehydrogenase as Safe Endpoint Cooking Indicator in Poultry Breast Rolls: Development of Monoclonal Antibodies and Application to Sandwich Enzyme–Linked Immunosorbent Assay," (ELISA), *Journal of Food Protection*, Feb., 1993, pp. 120–124, vol. 56(5).
Andrews, C.D., et al., "Detection of Beef, Sheep, Deer, and Horse Meat in Cooked Meat Products by Enzyme–Linked Immunosorbent Assay," *J. Of AOAC International*, May, 1992, pp. 572–576, vol. 75(3).
Billett, E.E., et al., "The Use of a Poultry–Specific Murine Monoclonal Antibody Directed to the Insoluble Muscle Protein Desmin in Meat Specification," *J. Sci. Food Agric.*, 1996 pp. 396–404, vol. 70.
Berger, R.G., et al., "Detection of Poultry and Pork in Cooked and Canned Meat Foods by Enzyme–Liked Immunosorbent Assays," *J. Assoc. of Anal. Chem.*, pp. 406–409, vol. 71(2).
Garcia, T., et al., Production of a Horse–Specific Monoclonal Antibody and Detection of Horse Meat in Raw Meat Mixtures by an Indirect ELISA, *J. Sci. Food Agric.*, pp. 411–415, vol. 66.

Hsieh, Y–H, P. et al., "Detection of Species Adulteration in Pork Products Using Agar–Gel Immunodiffusion and Enzyme–Linked Immunosorbent Assay," *Journal of Food Quality*, 1996, pp. 1–13, vol. 19.
Hsieh, Y–H., P., et al., Detection of Species Substitution in Raw and Cooked Meats Using Immunoassays, *Journal of Food Protection*, pp. 555–559, vol. 58(5).
Jones, S.J., and R.L. Patterson, "Double–Antibody ELISA for Detection of Trace Amounts of Pig Meat in Raw Meat Mixtures," *Meat Science*, 1985, pp. 1–13, vol. 15.
Martin, R., et al., "Monoclonal Antibody Sandwich ELISA for the Potential Detection of Chicken Meat in Mixtures of Raw Beef and Pork," *Meat Science*, 1991, pp. 23–31, vol. 30.
Martin, R., et al., "Production and Characterization of Monoclonal Antibodies Specific to Chicken Muscle Soluble Proteins," *Meat Science*, 1989, pp. 199–207, vol. 25.
Morales, P., et al., "Monoclonal Antibody Detection of Porcine Meat," *Journal of Food Protection*, Feb., 1994, pp. 146–149, vol. 57(2).
Patterson, R., and S.J. Jones, "Review of Current Techniques for the Verification of the Species Origin of Meat," *4 The Analyst*, May, 1990, pp. 501–506, vol. 115.
Smith, D.M., et al., Cooking Temperature of Turkey Ham Affects Lactate Dehydrogenase, Serum Albumin and Immunoglobulin G as Determined by ELISA, *Journal of Food Science*, 1996, pp. 209–212, Vol 61(1).
Townsend, W.E., and L.C. Blankenship, "Methods for Detecting Processing Temperatures of Previously Cooked Meat and Poultry Products—A Review," *Journal of Food Protection*, Feb., 1989, pp. 128–135, vol. 52(2).
Wang, C.–H., et al., "Antibody Development and Enzyme–Linked Immunosorbent Assay for the Protein Marker Lactate Dehydrogenase to Determine Safe Cooking End–Point Temperatures of Turkey Rolls," *J. Aric. Food Chem.*, 1992, pp. 1671–1676, vol. 40.
Wang, C.–H., et al., Lactate Dehydrogenase, Serum Protein and Immunoglobulin G Content of Uncured Turkey Thigh Rolls as Influenced by Enpoint Cooking Temperatures, *J. Agric. Food Chem.*, 1994, pp. 1829–1833, vol. 42.
Wang, C.–H., and D.M. Smith, Lactate Dehydrogenase Monoclonal Antibody Immunoassay for Detection of Turkey Meat in Beef and Pork, *Journal of Food Science*, 1995, pp. 253–256, vol. 60(2).
Wang, C.–H., et al., "Lactate Dehydrogenase Polyclonal Antibody Sandwich ELISA for Determination of Endpoint Heating Temperatures of Ground Beef," *Journal of Food Protection*, pp. 51–55, vol. 59(1).
Wang, C.–H., et al., "Proteins as Potential Endpoint Temperatures Indicators for Ground Beef Patties," *Journal of Food Science*, 1996, pp. 5–8, Vol 61(1).

* cited by examiner

Primary Examiner—Laurie Scheiner
(74) Attorney, Agent, or Firm—Alston & Bird LLP

(57) ABSTRACT

Monoclonal antibodies are provided which bind to heat-treated proteins of meats. The antibodies are useful in detecting the presence of an exogenous meat in a cooked or raw meat sample. Furthermore, the antibodies can be used to determine the end point temperature of a meat sample.

10 Claims, 14 Drawing Sheets

MONOCLONAL ANTIBODIES SPECIFIC TO COOKED MEATS

CROSS-REFERENCE TO RELATED APPLICATIONS

This application is a continuation of U.S. Divisional application Ser. No. 09/225,141, filed Jan. 4, 1999, which claims the benefit of U.S. application Ser. No. 08/906,851, filed Aug. 6, 1997, which claims the benefit of U.S. Provisional Application No. 60/024,887, filed Aug. 30, 1996, all of which are hereby incorporated herein in their entirety by reference.

FIELD OF THE INVENTION

The present invention relates to the development of monoclonal antibodies for the detection of meat species, particularly cooked meats, and for the end-point temperature of heat processed meat.

BACKGROUND OF THE INVENTION

The accurate labeling of meat products is mandated and monitored by the United States Department of Agriculture (USDA) as well as by state and local governments. Mixing undeclared species in meat products is illegal under Food Labeling Regulations. Apart from regulatory reasons, the prevention of adulteration of meat products with less desirable meat species is important to the consumers for economic, health, food safety and religious reasons.

Several methods have been developed to identify meat species including electrophoresis, chromatography, DNA hybridization, and immunoassays. Immunological techniques, including agar-gel immunodiffusion (AGID) and enzyme-linked immunosorbent assay (ELISA) are most commonly applied for meat species identification.

There are several disadvantages to the official method AGID. Concentrated antiserum preparations are required to obtain visible precipitin lines in AGID. Obtaining the antiserum is expensive in large-scale testing. Furthermore, the sensitivity of AGID is variable. Usually ten percent or more contamination must be present to detect adulteration with this method. Lastly, AGID cannot be used for species identification in cooked meat because of the shortage of commercial antiserum specific to cooked meats.

The ELISA method has emerged as a sensitive, rapid, and specific method for meat speciation. This method can detect levels as low as one percent or less of meat contamination. Furthermore, it requires only simple sample preparation and no expensive equipment or highly skilled operator. In addition, the ELISA technique can be used for both qualitative and quantitative analysis of meat proteins.

Specific antibodies, either polyclonal antibodies or monoclonal antibodies (MAbs), are required as capture reagents in ELISA. Most of the ELISA methods currently employed for meat species identification use polyclonal antibodies as a capture reagent. However, polyclonal antibodies have disadvantages such as limited production, variable affinity and a requirement for further purification to eliminate cross-reaction.

Using monoclonal antibody based ELISA can provide better data quality and eventually reduce the cost of assays. To date, the monoclonal antibodies which are utilized in ELISA based assays for meat identification have been raised against native proteins. The antibodies are useful for the detection of meat in raw meat mixtures.

A few disclosures of the production of polyclonal antibodies for the qualitative detection of meat species in cooked meat samples has been reported. These polyclonal antibodies have been raised against native heat-resistant immunizing antigens.

Wide spread meat species adulteration has been found particularly among heat-processed meat products and retail meat markets. Hsieh et al. (1995) *Jrnl. of Food Quality* 19:1–13, indicated that the violation rate in cooked products was higher than raw meats (22.9% versus 15.9%) in the domestic market. This adulteration can have serious health consequences. Poultry carries pathogens that cause foodborne diseases. Cooking poultry requires a minimum internal temperature of 71.1° C. (160° F.) to kill salmonella. Beef requires a minimum internal temperature of 68.3° C. (155° F) to kill *E. Coli* H7:0157. If a meat product like beef is contaminated with poultry meat, it might impose a potential health hazard due to the inadequate heat-processing even at a very low level of contamination.

Development of a suitable screening method to detect undeclared exogenous meat is important to comply with the food labeling regulation. Furthermore, a means for determining the adequate end-point cooking temperature for food safety is also important.

There is, therefore, needed a method for the determination of species identification in cooked meats as well as to determine the end-point cooking temperature of meats.

SUMMARY OF THE INVENTION

The present invention is drawn to antibodies, monoclonal antibodies or fragments thereof which bind to soluble heat-denatured, heat degraded meat proteins, or thermal-stable muscle protein as well as to methods for making such antibodies and their uses. The antibodies are capable of meat species identification in raw and cooked meats and thus, find use in the detection of species substitution in meats. Additionally, the monoclonal antibodies that react to heat-denatured proteins are useful as an indicator of end-point temperature for cooked meats. Kits containing the antibodies are also provided.

BRIEF DESCRIPTION OF THE DRAWINGS

FIG. 1 The specificity of MAb 6F7 to cooked meat determined by indirect ELISA. Data shown are the means of three readings. P: pork; B: beef; L: lamb, De: deer; H: horse; C: chicken; T: turkey, Du: duck.

DETAILED DESCRIPTION OF THE PREFERRED EMBODIMENTS

Figure 2:
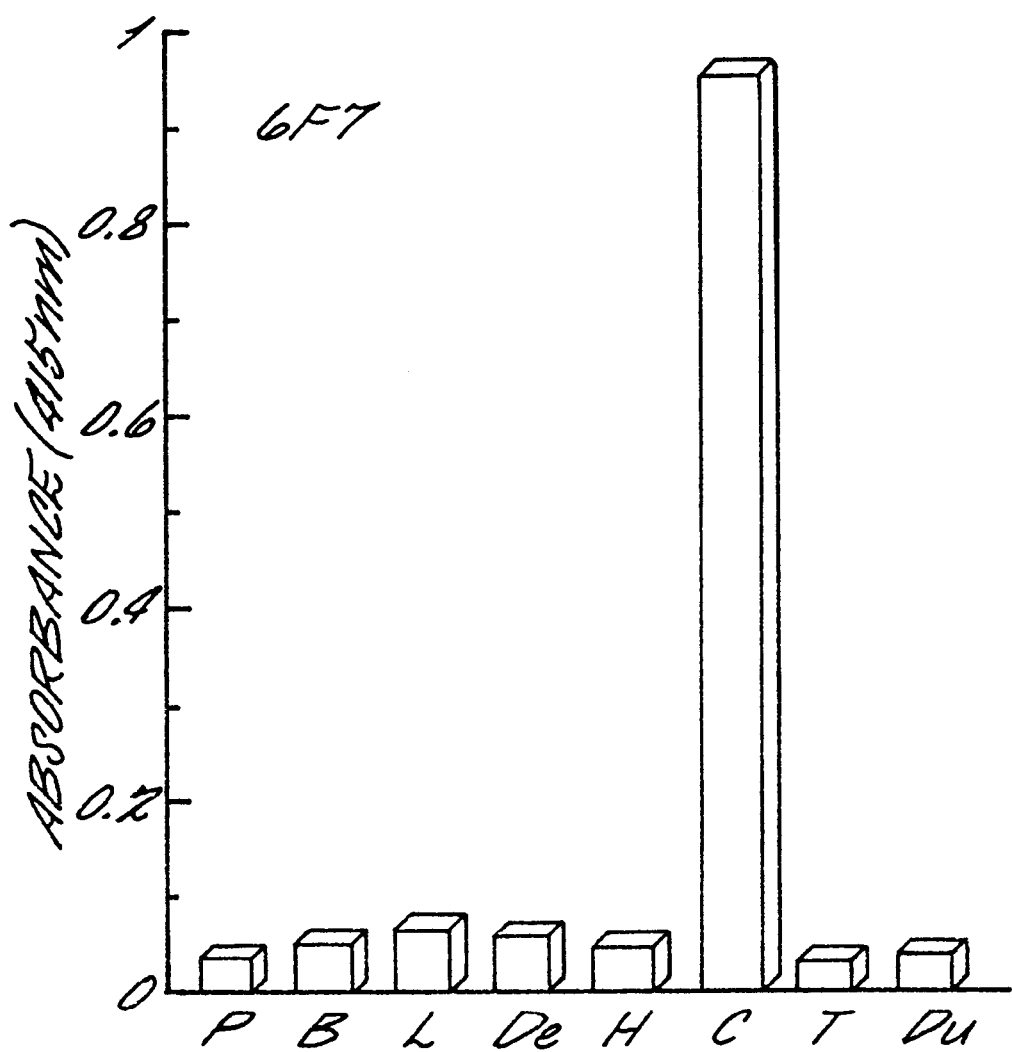
FIGS. 2A and 2B The specificity of MAbs 3E12 and 1A5 to cooked meat determined by indirect ELISA. Data shown are the means of three readings. P: pork; B: beef; L: lamb, De: deer; H: horse; C: chicken; T: turkey, Du: duck.
Figure 2A:
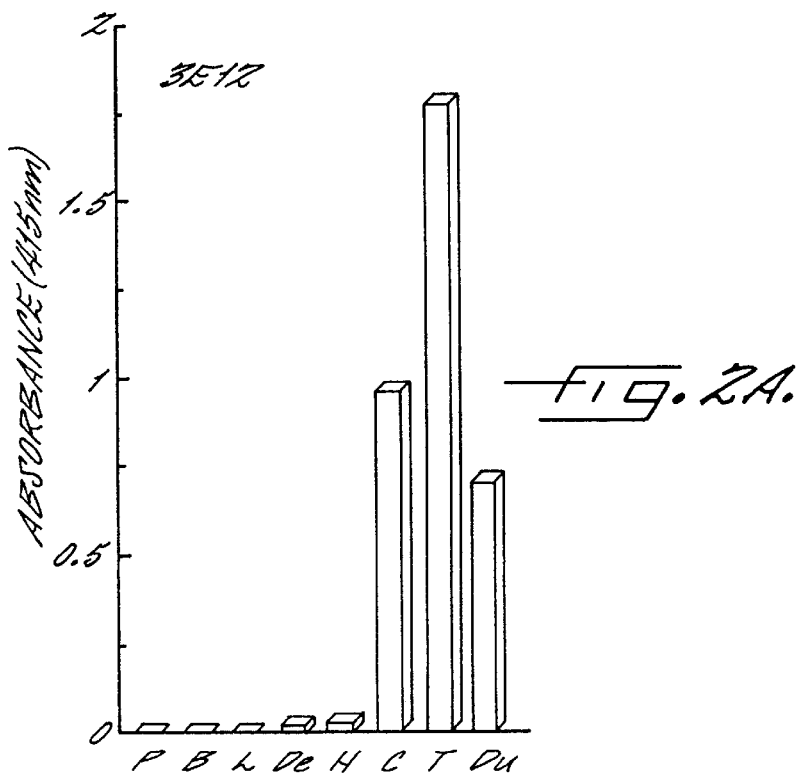
Figure 2B:
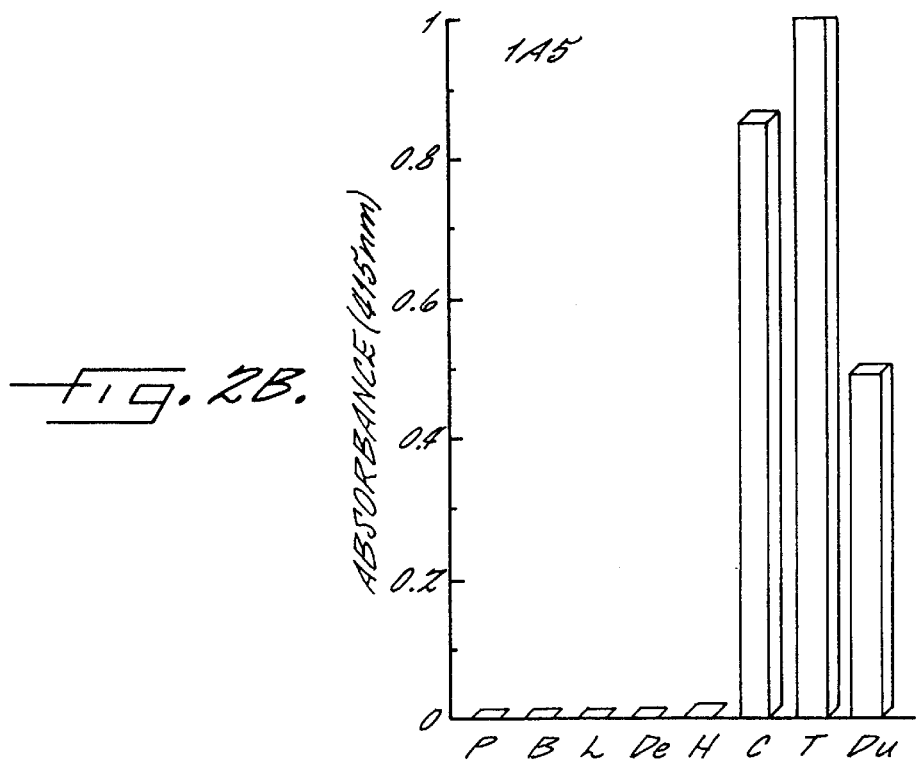

Antibodies and monoclonal antibodies, including fragments thereof which are capable of binding with the specificity of the antibody or monoclonal antibody, to soluble heat-denatured or heat degraded meat proteins are provided. Additionally, antibodies and monoclonal antibodies to thermal-stable muscle protein are provided. Such antibodies specifically bind to soluble heat-denatured or heat degraded proteins as well as to thermal-stable muscle proteins from meat and are capable of identifying particular meat types or meat species.

The antibodies of the invention include polyclonal and monoclonal antibodies as well as fragments thereof which retain the ability to bind to the heat-treated proteins from meat. Heat-treated proteins include heat degraded, heat-denatured soluble proteins as well as to thermal-stable muscle proteins from meat. An antibody, monoclonal antibody, or fragment thereof is said to be capable of binding to a molecule if it is capable of specifically reacting with the molecule to thereby bind the molecule to the antibody, monoclonal antibody, or fragment thereof. The term "antibody" (Ab) or "monoclonal antibody" (MAb) is meant to include intact molecules as well as fragments or binding regions or domains thereof (such as, for example, Fab and F(ab)$_2$ fragments) which are capable of binding antigen. Such fragments are typically produced by proteolytic cleavage, such as papin or pepsin. Alternatively, antigen-binding fragments can be produced through the application of recombinant DNA technology or through synthetic chemistry.

Methods for the preparation of the antibodies of the present invention are generally known in the art. For example, see Antibodies, A Laboratory Manual, Ed. Harlow & David Lane (eds.) Cold Spring Harbor Laboratory, N.Y. (1988), as well as the references cited therein. Standard reference works setting forth the general principles of immunology include: Klein, J. Immunology: The Science of Cell-Noncell Discrimination, John Wiley & Sons, N.Y. (1982); Dennett, R. et al. Monoclonal Antibodies, Hybridoma: A New Dimension In Biological Analyses Plenum Press, N.Y. (1980); and Campbell, A. "Monoclonal Antibody Technology," Laboratory Techniques In Biochemistry And Molecular Biology, Vol. 13, Burdon et al. (eds.), Elsevier, Amsterdam (1984). See also, U.S. Patent Nos: 4,609,893; 4,713,325; 4,714,681; 4,716,111; 4,716,117; and 4,720,459.

The antibody and monoclonal antibodies of the present invention can be prepared by various methods. One method to obtain antibodies to heat-degraded or heat-denatured proteins utilizes heat-treated (100° C., 15 min.) soluble meat proteins as antigen. Such soluble proteins can be prepared by blending a sample of meat from a species of interest, adding a solution, generally saline to the blended meat, followed by heating, e.g. boiling, the homogenate. The soluble proteins are then extracted by gentle agitation followed by centrifugation and filtration. The supernatant contains the protein extract which can be used to immunize mice.

Another antibody preparation method utilizes thermal-stable muscle protein as antigen. Such thermal-stable proteins can be prepared by modifying the method of Milgrom and Witebsky (1962), Immunology 5:46–66, herein incorporated by reference. Generally, after removing fat and connective tissue, muscle tissue is homogenized, sonicated and heated to boiling. The mixture is centrifuged; the supernatant collected, autoclaved, and filtered to remove debris and proteins precipitated by using, for example, ethanol. The precipitate is dried and can be used to immunize an animal, i.e., mice, for the production of antibodies.

A critical aspect of the invention involves the selection of antibodies or monoclonal antibodies made by the above method by indirect ELISA. In performing the indirect ELISA assays, the soluble protein antigen is bound to a polyvinyl surface. The polyvinyl surface is capable of binding the heat-treated soluble meat (denatured or degraded) proteins better than other materials tested, such as polyethylene plates. Until the present invention, this had not been recognized in the prior art resulting in false negative readings for antibody production.

By the method of the invention described herein, monoclonal antibodies having a desired specificity can be selected. Thus, monoclonal antibodies specific for a particular meat species or for a type or class of meats can be produced.

By meat type or class is intended a broader class of meats including several meat species. Thus, type or class refers to mammalian, poultry, and the like. By meat or meat species is generally intended meats which are commonly used for consumption, including poultry such as chicken, turkey, and duck, and mammalian meats, such as pork, beef, lamb, deer, and horse. Thus, particular meat species include but are not limited to chicken, turkey, duck, pork, beef, lamb, deer, horse, and the like. It is recognized that the method of the invention could be utilized to obtain antibodies against any meat species.

The methods of the invention can be used to develop antibodies which are capable of identifying classes of meats, for example, mammalian verses poultry, as well as to identify the particular meat species. In this manner, the antibodies of the invention are useful for meat type or class as well as particular meat species identification.

Two broad types or classes of antibodies or monoclonal antibodies may be prepared by the methods described above.

One type encompasses antibodies which bind thermal-stable proteins. Such antibodies are capable of binding to both cooked and raw meat samples. Thus, these antibodies are useful for identification of meats in both raw and cooked meat samples.

The second type of antibodies and monoclonal antibodies of the invention are capable of binding cooked meat samples. However, it is recognized that for species identification, both raw and cooked meats can be utilized in the invention. Where the sample of the meat is raw, a heat denaturing step will be needed. Accordingly, the sample can be heated, i.e., boiled, prior to contacting the sample with the antibody.

Because the antibodies are both meat and class specific, they are useful in the detection of species substitution in meats. To facilitate their use, kits containing the antibodies can be made. The antibodies can be coated onto a solid phase, such as ELISA microliter plate, dipstick, magnetic beads, and the like, and used as a sensitive reagent to accurately detect a meat of interest in both cooked and raw meat products. This commercial kit form is useful for rapid and convenient use by regulatory agencies and the meat industry. By "kit" is intended that the monoclonal antibody and any necessary reagents are contained in close confinement in the form of a ready-to-use test kit. The antibodies of the invention are useful in non-competitive ELISA, including double-sandwich ELISA assays as well as competitive assays. However, other formats such as homogenous enzyme immunoassays may be developed.

The second type of antibodies or monoclonal antibodies of the invention also find use as indicators of end-point temperature of a cooked meat sample. Inadequate cooking is an important contributing factor in foodborne disease outbreaks caused by meat products. The second type of antibodies are developed against heat-denatured or heat degraded soluble proteins. Heat induces conformational changes of the protein molecules. In this manner, end-point temperature can be determined by using the antibody in an ELISA to detect the immunoreactivity changes of the heat treated muscle proteins. An increase in reactivity is noted due to increased heating process of the meat sample. The antibody allows for a means to determine end-point temperature to which beef and poultry have been processed.

Preferred embodiments of the invention include the following monoclonal antibodies which have been developed using heat-denatured or heat degraded proteins as antigens.

The monoclonal antibody 2F8, produced by hybridoma cell line 2F8 deposited as ATCC No. HB-12155, reacts with five commonly used mammalian cooked meats, pork, beef, lamb, horse and deer. The monoclonal antibody can be used as a capture reagent in ELISA to detect any of the five mammalian meats in a sample. The monoclonal antibody is particularly useful to identify meat adulteration of any of the five mammalian meats in a poultry product. It also finds use in determining the end-point cooking temperature for mammalian meats.

In another preferred embodiment, five monoclonal antibodies specific to cooked chicken muscle soluble proteins have been developed. These monoclonal antibodies represent three groups of cell lines which secret monoclonal antibodies to specifically react with heat denatured poultry meats. The first group of monoclonal antibodies are represented by the monoclonal antibody 3E12, produced by hybridoma cell line 3E12, deposited as ATCC No. HB-12154, are capable of distinguishing between cooked poultry meats (chicken, turkey and duck) and cooked land animal meats (pork, beef, lamb, deer and horse).

The second group of monoclonal antibodies represented by 6F7, produced by hybridoma cell line 6F7, react with cooked chicken without any cross-reaction to any other species tested. They are useful to distinguish chicken tissue from other non-chicken meats.

The third group of monoclonal antibodies represented by 5D2, produced by hybridoma cell line 5D2 deposited as ATCC No. HB-12156, react with both cooked chicken and turkey but not with other meat species.

All three classes of monoclonal antibodies react with cooked poultry proteins. However, the monoclonal antibodies can be used in testing raw meats as well as cooked meat products. For the analysis of raw meats, an additional heat treatment is required for sample preparation. The monoclonal antibodies can be used as a capture reagent in ELISA to detect poultry meats in a sample. They also find use in determining the adequate end-point cooking temperature for poultry meats.

The antigens for preparation of the above specifically listed antibodies are soluble heat-denatured or degraded protein or peptide units. Most of them are low molecular weight proteins/peptides having a molecular weight in the range of up to about 35 kd. In the heating process, some muscle proteins are degraded into smaller units, most are denatured and many become insoluble. See, generally Tajima et al. (1991) *J. Home Econ. Jpn.* 42:967–971. The extract which is used as an immunogen is a crude soluble protein extract which has been heat treated. The use of the crude extract increases the number of species-specific antibodies which are produced. Particular antibodies can be selected based on binding characteristics.

Another preferred embodiment of the invention includes monoclonal antibodies prepared using thermal-stable muscle soluble proteins as antigens. The monoclonal antibody 5H9, produced by hybridoma cell line 5H9 deposited as ATCC No. HB-12245, reacts specifically with raw and cooked pork. No significant cross-reactivity is found among other meats including beef, lamb, horse, deer, chicken, turkey, and duck. Antibody 5H9 is useful for detecting pork in a heterogeneous meat sample.

The MAb 5H9 recognizes three protein bands with apparent molecular weights about 24, about 22 and about 20.5 kd in raw pork but recognizes one protein band of about 24 kd in cooked pork. The 24 kd protein was identified as a species specific thermo stable muscle protein.

The following experiments are offered by way of illustration and not by way of limitation.

Experimental

EXAMPLE 1

Materials and Methods

Extraction of Cooked Meat Soluble Proteins

Lamb, turkey and duck meat were purchased from a local supermarket. Pork, beef and chicken meat were obtained from the Auburn University Meats Laboratory. Horse and deer meats were obtained from the College of Veterinary Medicine, Auburn University.

Extraction of soluble proteins was performed as follows. Thirty grams of meat from each species were cut into small pieces and blended separately by blender (Virtis Model 45, Gardiner, N.Y.) for one minute. Three fold (w/v) of saline solution (0.85% NaCl) was added to the blended meat. The homogenate was cooked by boiling at 100° C. for fifteen minutes. The soluble proteins were extracted by gentle agitation for two hours at 4° C. then centrifuged at 14,300×g for thirty minutes at 4° C. (Beckman J-21C, Palo Alto, Calif.). Supernatants were filtered through Whatman No. 1 filter paper (Maidstone, Kent, England) and stored at −80° C. until use.

The protein concentration of extracts was determined by protein assay kit II(Bio-Rad, Hercules, Calif.) based on the method of Bradford (1976). Bovine serum albumin was used as standard in this assay.

Immunization

Four ten-week-old female BALB/c mice (PRN 9612-R-0597) were immunized with the crude protein extract of cooked chicken. Mice were injected intraperitoneally or subcutaneously with an emulsion containing 100 µl of antigen (0.5 µg/µl of cooked chicken protein) and 100 µl of complete Freund's adjuvant (Sigma, St. Louis, Mo.). Three weeks later, mice were boosted with the same dose of antigen emulsified in incomplete Freund's adjuvant (Sigma). One week after, sera were collected from mice by tail vein bleeding. The sera were used to test the antibody titers against antigen using indirect ELISA. A final booster was done four days before fusion by injecting 200 µl of 0.01 M phosphate buffered saline (PBS), pH 7.2 containing 50 µg of cooked chicken antigen into the mouse which had the highest antibody titer.

Production of Monoclonal Antibodies

Peritoneal macrophages were collected as feeder cells one day before fusion. Four days after the final booster, the injected mouse was sacrificed, and the spleen was harvested. Cells were washed from spleen by wash media (RPMI-1640 serum free medium supplemented with 1% oxaloacetate, pyruvate, and insulin (OPI) containing 1% glutamine, and 1% penicillin and streptomycin (p/s))(Sigma). Cells of the murine myeloma cell line, P3X63, Ag8.653, ATCC CRL 1580 were retrieved from liquid nitrogen and cultured in large tissue culture plates (Corning, Corning, N.Y.). The culture procedure is described in Procedure A (page 31). The spleen cells were fused with myeloma cell line Ag8.653 in a 2:1 ratio using 50% polyethylene glycol (PEG) 4000 (Sigma) as the fusion agent. One ml of 50% PEG was gently added to the cells dropwise. After standing for one minute, 30 ml of wash media was added to cells dropwise. The fused cells were resuspended in Hypoxanthine-aminopterin-thymidine (HAT) selective growth medium (RPMI-1640 supplemented with 15% fetal bovine serum (FBS), 1% OPI, 1% glutamine, 1% p/s, 1% HAT) (Sigma) and seeded in 96-well tissue culture plates that have been set with mouse thymocyte feeder cells (Kohler and Milstein, 1975). The hybridoma cells were incubated at 37° C. with 5% $CO_2$ (Napco $CO_2$ incubator model 6300, Tualatin, Oreg.).

The supernatants of hybridoma cells were screened by indirect ELISA against cooked chicken antigen. Hybridoma cells from the positive wells were expanded to 48-well plates and collected supernatants to test against protein extracts from cooked pork, beef, lamb, deer, horse, chicken, turkey and duck for cross-reactivity.

Antibody-producing hybridoma cells of interest were selected and recloned twice by limiting dilution (Campbell, 1991). Cells were diluted with complete growth media (RPMI-1640 supplemented with 15% FBS, 1% OPI, 1% glutamine and 1% p/s) to give a concentration of 0.5 or 1 cell per well. Two hundred µl of each dilution were plated in each well to 96-well plates seeded with mouse thymocyte feeder cells. The subcloned hybridoma cells were screened using the method described previously.

The antibody-producing hybridoma cells were expanded from 96-well plate to 48-well plate. When the cells grew heavily in the well, they were expanded to 24-well plate, 12-well plate, small petri culture dish and large petri culture dish, sequentially. When cells grew heavily in the large petri dish, they could be frozen and stored in liquid nitrogen (Procedure B, page 32).

ELISA

Two µg of chicken antigen or protein extracts from the eight cooked meat species in 100 µl of carbonate buffer (0.06 M pH 9.6) was coated to each well of a 96-well round-bottomed vinyl microtiter plate (Costar, Cambridge, Mass.) and incubated for 1 h at 37° C. or at 4° C. overnight. After washing three times with 0.01 M phosphate buffered saline, pH 7.2, containing 0.5% Tween-20 (PBST) using an immunowash microplate washer (Bio-Rad model 1250), 100 µl of 10% bovine serum albumin (Sigma) in PBS were added to each well to block nonspecific binding sites. Following incubation for 1 h at 37° C., the plate was rinsed three times with PBST, and 100 µl of hybridoma cell supernatant were then added to each well and incubated for 1 h at 37° C., and an additional hour at room temperature. After washing the plate with PBST three times, 100 µl of diluted (1:3000 in PBS) horseradish peroxidase conjugated goat anti-mouse IgG (H+L) (Bio-Rad) was added and the plates were incubated for 1 h at 37° C. The plate was washed with PBST three times and 100 µl of substrate solution containing 2,2'-azino-di-[3-ethyl-bezthiazoline-6-sulfonic acid] and hydrogen peroxide (Bio-Rad) was added to each well. The plate was incubated for ten minutes at 37° C. The reaction was stopped by adding 50 µl of 10% oxalic acid and the absorbance was read in a microplate reader (Bio-Rad model 450) at 415 nm.

Isotyping of MAb

The isotype of MAb was determined by a mouse monoclonal antibody isotyping kit according to manufacture's manual (Sigma).

Concentrating of Protein Extracts

Protein extracts of cooked meats were concentrated by ultrafiltration (Model 8050, Amicon, Beverly, Mass.) using a YM-10 membrane (Amicon). Nitrogen was applied to the system at 2114 g/cm² to facilitate the filtration process.

SDS-PAGE and Western Blot

Sodium dodecyl sulfate-polyacrylamide gel electrophoresis (SDS-PAGE) was performed to resolve the protein extracts of different cooked meat species. Western blot was then carried out to transfer proteins from gel to nitrocellulose membrane and to determine the molecular weights of immunogenic components which reacted with developed MAbs. Sodium dodecyl sulfate-polyacrylamide gel electrophoresis was performed according to the method of Laemmli (1970) with the following modifications. Proteins were separated on 4% acrylamide stacking gel (pH 6.8) and a 12% acrylamide separating gel (pH 8.8). The protein extracts of different cooked meat species were diluted one-half with sample buffer containing 2% (wt/vol) SDS, 5% (vol/vol) β-mercaptoethanol, 60 mM Tris hydrochloride (pH 6.8), 25% (vol/vol) glycerol and 0.0001% (wt/vol) bromophenol blue (Laemmli, 1970), boiled for 2 minutes, cooled, and applied to the gel at 10 µg/well. The gel was electrophoresed at 200 V for 45 minutes using a Protean-II minigel system (Bio-Rad) connected to a power supply (Bio-Rad Model 3000). After electrophoresis, the resolved protein bands were transferred to nitrocellulose membranes (Bio-Rad) at 100 V for 1 hour using an electroblotting apparatus (Bio-Rad) in blotting buffer (20 mM Tris, 250 mM glycine, 20% methanol) according to the method of Towbin et al. (1979). Upon completion of the electroblotting, the nitrocellulose membrane was blocked by 3% gelatin (Bio-Rad) in PBS for 30 minutes. Following two washes in Tris-buffered saline with Tween (TBST) (TBS, pH 7.5, containing 0.05% Tween-20), the membrane was incubated with hybridoma supernatant in antibody buffer (1% gelatin in TBST) overnight at room temperature. The excess MAb was removed by washing twice with TBS, and the membrane was incubated with goat anti-mouse IgG alkaline phosphatase conjugate diluted in antibody buffer (1:3000) for 1 hr at room temperature. After washing with TBST two times, and an additional wash with TBS, the membrane was incubated with 5-bromo-4-chloro-3-indolyl phosphate/p-nitroblue tetrazolium chloride (BCIP/NBT) in alkaline phosphatase color development solution (0.1 M, pH 9.5 Tris buffer)(Bio-Rad). The reaction was stopped by washing the membrane in distilled water. The appearance of a dark purple band indicated the antibody binding site. The prestained PAGE broad range standards including myosin (M. Wt. 205,000), β-galactosidase (M. Wt. 116,500), bovine serum albumin (M. Wt. 80,000), ovalbumin (M. Wt. 49,500), carbonic anhydrase (M. Wt. 32,500), soybean trypsin inhibitor (M. Wt. 27,500), lysozyme (M. Wt. 18,500) and aprotinin (M. Wt. 6,500) were used as molecular weight markers in SDS-PAGE and Western immunoblotting.

Preparation of Adulteration Standards

The protein extracts of cooked chicken, turkey or duck were used as adulterants to cooked pork or beef. Different percentage (vol/vol) of adulterating protein extracts were mixed with pure protein extract of cooked pork. Protein concentration was calculated for each mixture according to the amount of protein in each pulte protein extract. Each mixture was diluted in carbonate buffer (0.06 M pH 9.6) to the protein concentration of 2 μg/100 μl and used as antigen in ELISA.

Results and Discussion

Figure 3A:
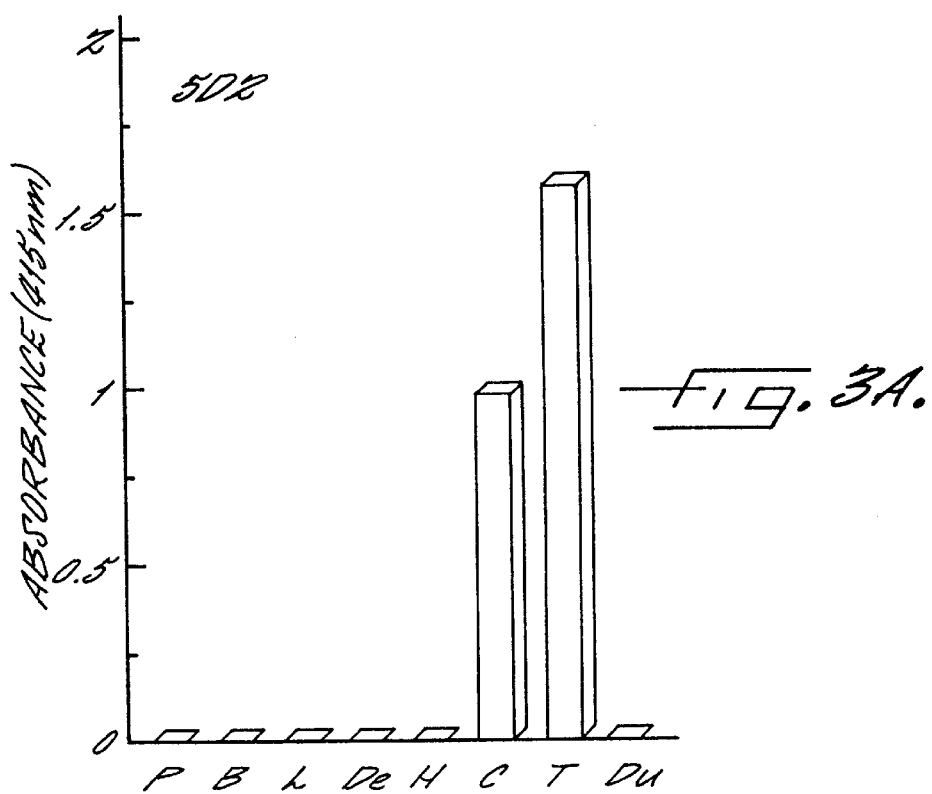
FIGS. 3A and 3B The specificity of MAbs 5D2 and 6G8 to cooked meat determined by indirect ELISA. Data shown are the means of three readings. P: pork; B: beef; L: lamb, De: deer; H: horse; C: chicken; T: turkey, Du: duck.
Figure 3B:
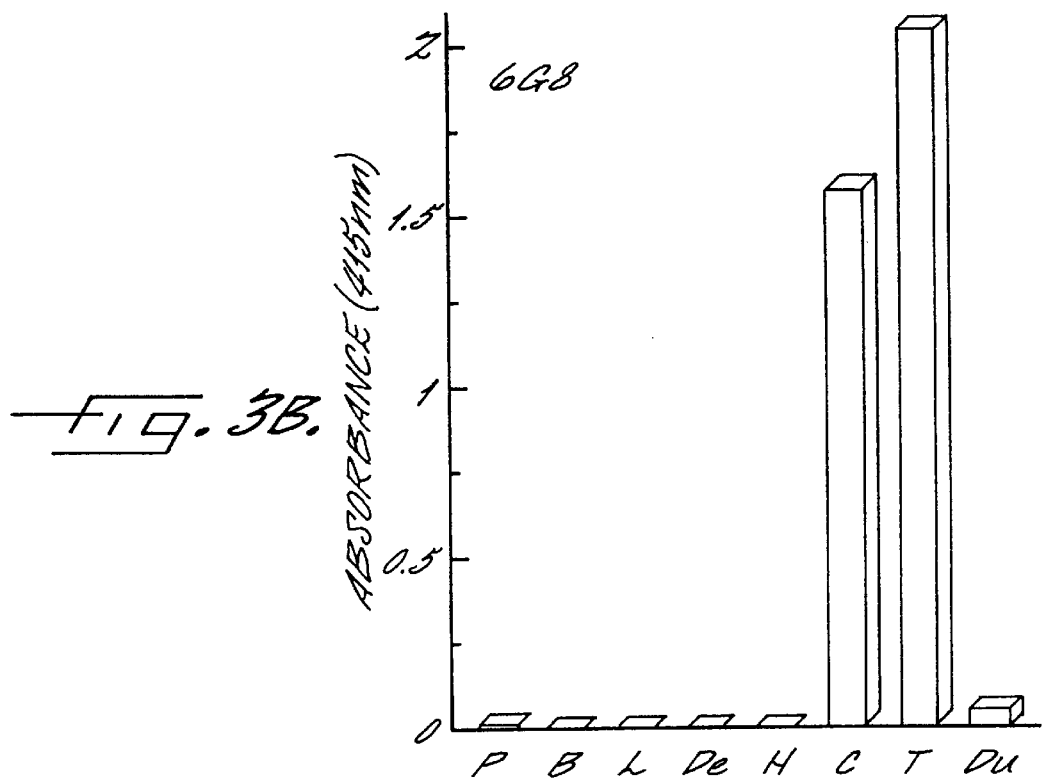

Soluble muscle crude protein extract of cooked chicken was used as the antigen to immunize mice. Sera of all four immunized mice showed very high titers of antibodies against the antigen. Only the mouse showing the highest titer was sacrificed for fusion. Screening supernatants of hybridoma clones by indirect ELISA illustrated that a number of clones produced MAbs against cooked chicken antigen. Only the positive clones giving strong positive indirect ELISA were expanded to 48-well plates to obtain enough supernatant for testing against cross-reaction to other species (pork, beef, lamb, deer, horse, turkey and duck). One hundred and sixty-six clones were expanded and tested for cross reactivity and six were chosen for further study. When the six hybridoma cell lines were tested against cooked protein extracts of all species, MAbs secreted by cell line 6F7 were specific to chicken without noticeable cross-reactivity to pork, beef, lamb, deer, horse, turkey and duck was shown (FIG. 1). Hybridoma cell lines, 3E12 and 1A5, secreted MAbs specific to all three poultry muscle proteins (chicken, turkey and duck). There was no cross-reactivity to the five cooked mammalian meats for both MAbs (FIG. 2). Two other hybridoma cell lines, 5D2 and 6G8, secreted MAbs specific to cooked chicken and turkey. They showed no cross-reactivity to duck or five mammalian meats (FIG. 3).

The titers of the supernatants of these five hybridoma cell lines were determined by indirect ELISA (Table 1). The protein extracts of species that MAbs could react with were coated as antigens at 2 μg/100 μl to the ELISA plates. The titer was represented as the highest dilution fold of supernatant where absorbance was higher than 0.1. Although MAbs 3E12 and 1A5 reacted to all three cooked poultry muscle proteins, the reaction intensity among these three species were different. Both MAbs showed the highest reactivity to turkey, followed by chicken and the lowest to duck. For MAb 5D2 which was specific to cooked chicken and turkey, the reaction titer for cooked turkey was higher than cooked chicken. Monoclonal antibody 6G8 showed the highest reactivity to cooked chicken and turkey among five MAbs and the reaction intensity was similar for both species for MAb 6G8.

All these 5 MAbs were IgG class MAbs. Four of the five hybridoma cell lines secreted IgG class MAbs subclass IgG1. Only the cell line 6F7 secreted IgG class MAb subclass IgG2b (Table 2).

Protein extracts of eight species of cooked meats were resolved by 12% SDS-PAGE and detected by Coomassie-blue staining (not shown). The results showed that extracts of three poultry species had similar protein patterns. At least fourteen, sixteen and nine protein bands were seen in the SDS-gel pattern of cooked chicken, turkey and duck protein extracts, respectively.

Figure 4:
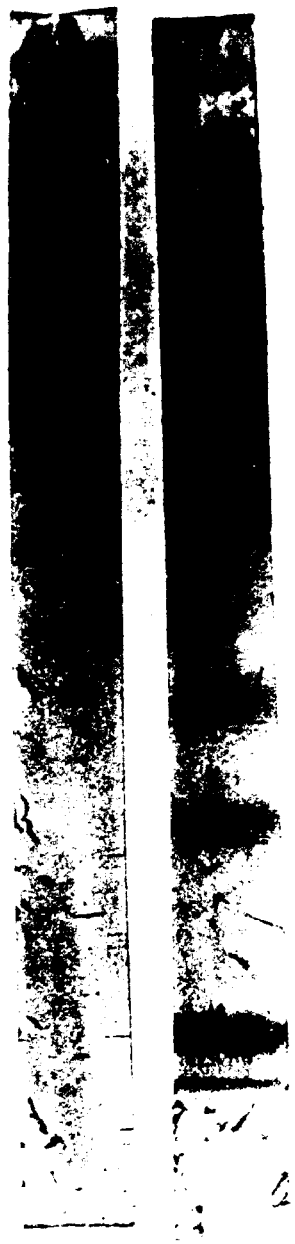
FIG. 4 Immunoblots of proteins extracted from cooked chicken separated on 12% (w/v) SDS-PAGE. Lanes; 1=reacted with 6F7, 2=prestained molecular weight standard.
Figure 5:
FIG. 5 Immunoblots of proteins extracted from cooked chicken, turkey and duck separated on 12% (w/v) SDS-PAGE. Lanes; 1 and 5=chicken, 2 and 6=turkey, 3 and 7=duck, 4 and 8=molecular weight standard. Lanes 1 to 4 were reacted with MAb 3E12. Lane 5 to 8 were reacted with MAb 1A5.
Figure 6:
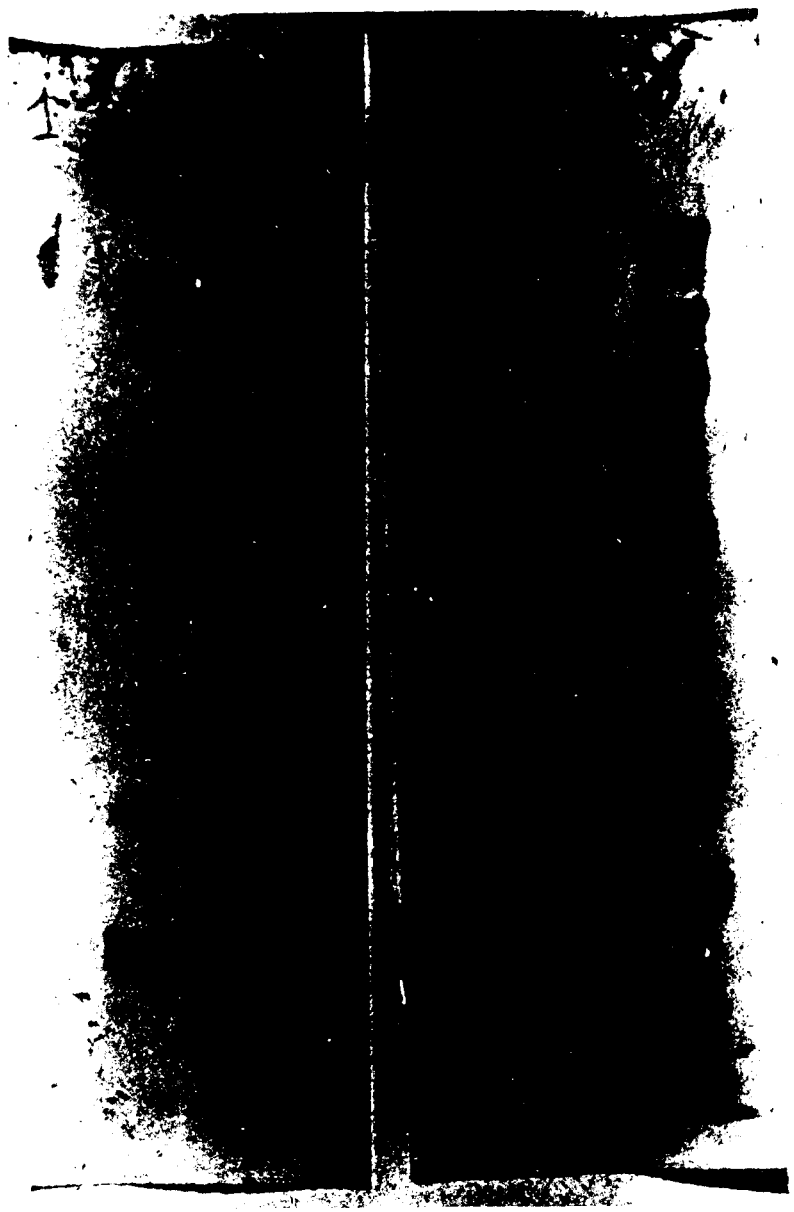
FIG. 6 Immunoblots proteins extracted from cooked chicken and turkey separated on 12% (w/v) SDS-PAGE. Lanes; 1 and 3=chicken, 2 and 4=turkey, 5=molecular weight standard. Lanes 1 and 2 were reacted with MAb 5D2. Lane 3 and 4 were reacted with MAb 6G8.

Protein extracts of three poultry species were separated by 12% SDS-PAGE. The resolved protein bands were transferred to a nitrocellulose membrane and detected using the undiluted supernatants containing MAbs to determine the immunogenic components in the protein extracts. The immunoblot of MAb 6F7 is shown in FIG. 4. A major band at 120 kDa in the protein extract of cooked chicken was found to react with MAb 6F7. Many minor continuous bands below 120 kDa also reacted with the MAb. The immunoblot shown in FIG. 5, shows that MAbs 3E12 and 1A5 shared the same sizes of proteins in all the three poultry species. The proteins detected by both MAbs in cooked chicken protein extract were located within 34, 30, 25 and 24 kDa. In turkey, two major bands at 29 and 22 kDa and two lesser reactive bands at 30 and 23.5 kDa were found. There was only one band at 30 kDa in duck protein extract which reacted with MAbs 3E12 and 1A5. For MAbs 5D2 and 6G8, the immunoblot indicated that the sizes of proteins which reacted with these two MAbs were the same (FIG. 6). Within chicken protein extract, there were three strong bands located at 30, 25 and 23.5 kDa and a lesser reactive band at about 35 kDa. There were strong reactions to 26 and 24.5 kDa bands in turkey protein extract for both MAbs. Two other immunoactive bands were also present at 29.5 and 22 kDa. The result of immunoblots for these five MAbs is summarized in Table 3.

Meat adulterated samples were prepared by substituting pure cooked pork protein extract with different poultry protein extracts at 0, 0.1, 0.5, 1, 5, 10, 20, 30, 40, 50, 60, 80 and 100% (vol/vol) levels. All the meat adulterants were diluted to the same concentration (2 μg/100 μl) then coated to the ELISA plate. The indirect ELISA using the undiluted supernatants containing MAbs was employed to quantify the substitution of pork with chicken, turkey or duck in the prepared adulterated meats. Monoclonal antibody 3E12 and 5D2 could detect the presence of 10% or less of chicken meat in pork and/or beef. The absorbance increased as the substitution of poultry meats for pork in the test meat extracts increased. Both of these two MAbs could detect 0–100% of poultry meats in a non-poultry meat sample. Zero to 100 percent of either chicken or turkey could be quantitatively detected using these two MAbs in both competitive and noncompetitive ELISA.

Figure 14:
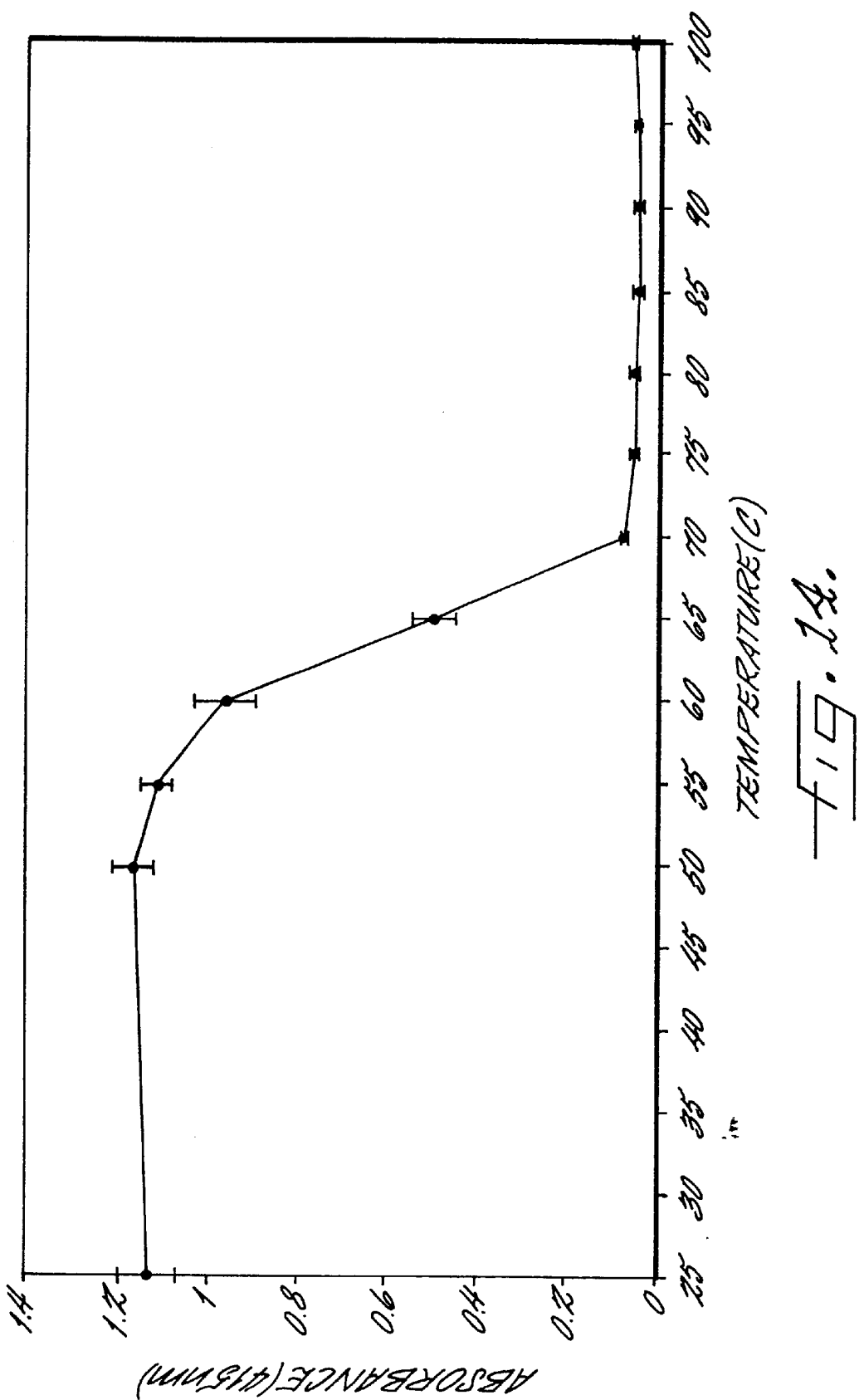
FIG. 14 Indirect competitive ELISA response of Mab 5D2 to protein extract from chicken breast cooked to different end-point temperature (EPT).
Figure 15:
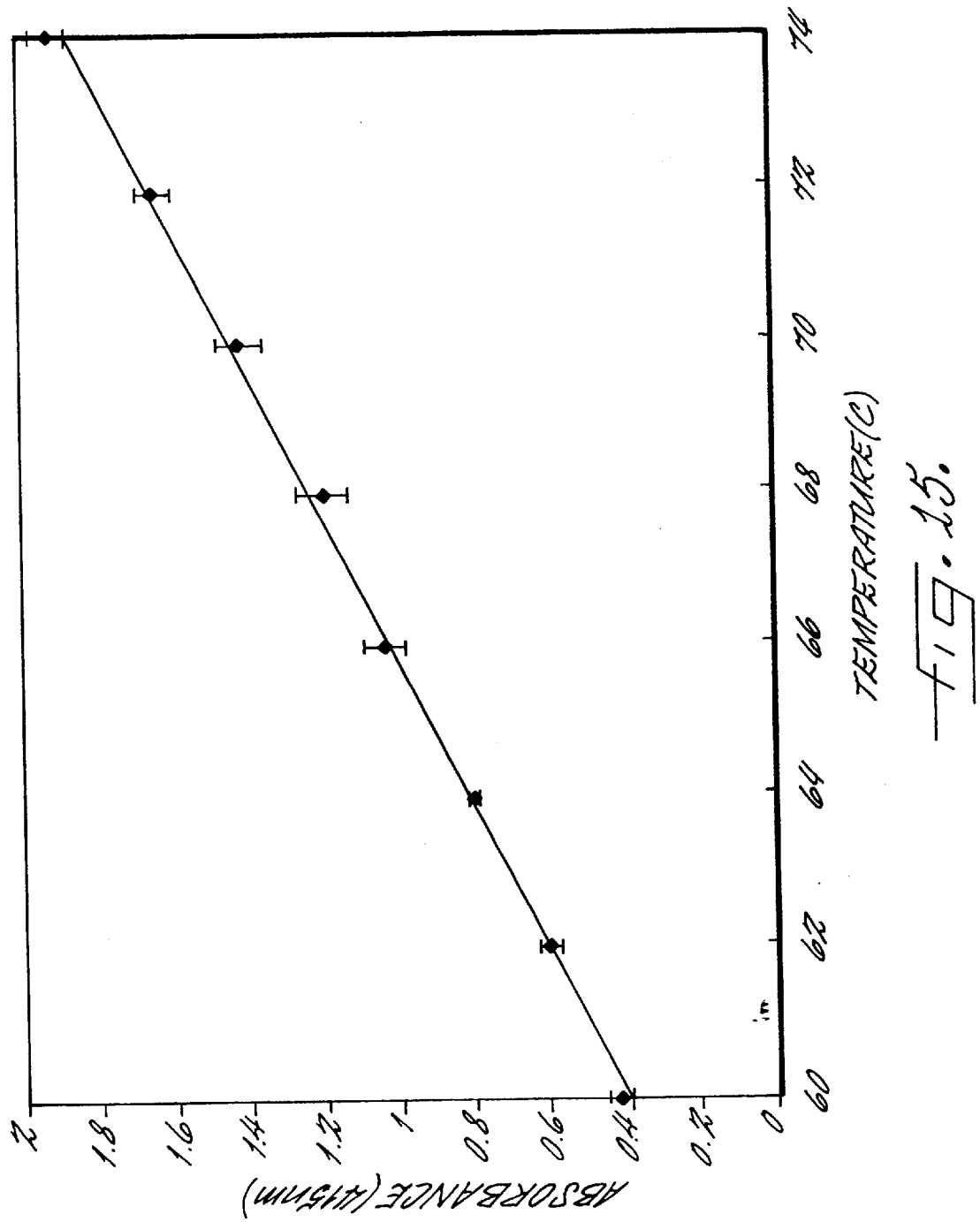
FIG. 15 Indirect ELISA response of Mab 5D2 to protein extract from chicken breast to different end-point temperature (EPT).

In addition using MAb 5D2 to determine end-point temperature of chicken with both competitive and non-competitive ELISA was feasible. Two representative figures are included to demonstrate use of these MAb. See FIGS. 14 and 15.

It is not suitable to develop MAbs against native proteins for species identification of cooked samples because heat treatments result in protein denaturation or degradation. Therefore, a group of heat-denatured or heat degraded components derived from tissue are required to detect species in cooked meat. Crude cooked chicken soluble muscle proteins were used as antigens to produce MAbs. The results demonstrated that it does not necessarily require purified antigens as a prerequisite to develop species-specific MAbs.

One hybridoma cell line of each reaction pattern was chosen to produce large amounts of antibodies in ascites fluids. The titers of these ascites fluids were tested. Titers 1:200 was determined as suitable in indirect ELISA format while titer 1:6400 was chosen for competitive ELISA format.

Muscle proteins not blood serum proteins (serum albumin) were used as antigens to produce MAbs in this study. The blood proteins are used to raise polyclonal antibodies in commercial raw meat species identification kits. Their quantity in a given sample does not necessarily parallel the amount of the corresponding species meat (Jones and Patterson (1988). Recent Developments in Meat Specification. In *Immunoassays for Veterinary and Food Analysis*-1, B. A. Morris, M. N. Clifford and R. Jackman (Ed),p. 121–126. Elsevier Applied Science Publishers, London, England). The amount of serum proteins is affected by the residual blood left in the muscle after slaughter (Warris (1977) *Meat Sci.* 2:155–159). Therefore, the presence of serum proteins does not essentially denote the amount of the corresponding muscle tissue. In contrast to serum proteins, the amount of muscle protein is proportional to the presence of lean meat. It is suitable to be used for both qualitative and quantitative analysis in meat species identification (Martin et al. (1991) *Meat Sci.* 30:23–31).

Detection of small amounts of substituted meat supplies is a concern of consumers and regulatory agencies. The present assay was adequate to illustrate a quantitative detection over a wide range of mixture levels (0–100%). Development of a sandwich ELISA or the use of an avidin-biotin immunoassay (Klein (1990) Antigen-antibody interactions. In *Immunology*, p. 294–310. Blackwell Scientific Publications, Oxford, England) would increase the sensitivity of the developed MAbs to quantify poultry adulterant in red meat products.

Poultry may be added into pork product due to the similar light color. The unmarketable trimmings of poultry may also be substituted into other red meats. Poultry requires a minimal internal temperature of 71.1° C. to kill Salmonella. (USDA-FSIS (1994) Requirements for the production of poultry breakfast strips, poultry rolls, and certain other poultry products. Animals and Animal Products. Part 381.150,p. 495496 of Chapter III. Title 9 of the Code of Federal Regulations, Office of the Federal Register, National Archives and Records, Washington, D.C.). If beef or lamb product contaminated with poultry was not fully cooked, it might cause Salmonellosis. Hsieh et al. (1995) reported that 18% and 38% of ground pork and pork sausage samples analyzed were contaminated with poultry using ELISA, respectively. About 31% of ground beef and ground veal samples was also contaminated with poultry (Hsieh et al. (1995) *J. Food Prot.* 58:555–559). A high percentage of adulteration with multiple species was also found in the ground pork and ground beef samples. The developed MAbs 3E12 and 1A5 could react with three poultry species and MAbs 5D2 and 6G8 could react with chicken and turkey. Therefore, these MAbs could be used in ELISA to detect the presence of poultry as a group in the cooked red meat products in a single test. It would be highly suitable and economical for an initial rapid screening of meat samples. Then MAbs 6F7 could be used for the specific identification of chicken adulterant in a positive sample. Furthermore, a convenient field test kit could be developed using these MAbs for meat inspectors.

TABLE 1

Titration of monoclonal antibodies against cooked poultry by indirect ELISA[a]

| MAbs | chicken | turkey | duck |
| --- | --- | --- | --- |
| 6F7  | 128 | — | — |
| 3E12 | 64  | 256 | 32 |
| 1A5  | 64  | 128 | 32 |
| 5D2  | 64  | 128 | ND |
| 6G8  | 512 | 512 | ND |

[a]Titers were represented as the highest dilution of supernatants that had absorbance above 0.1.

TABLE 2

The isotypes of MAbs specific to cooked poultry

| MAbs | Ig isotype |
| --- | --- |
| 6F7  | IgG2b |
| 3E12 | IgG1 |
| 1A5  | IgG1 |
| 5D2  | IgG1 |
| 6G8  | IgG1 |

TABLE 3

Immunogenic components of SDS-PAGE-separated proteins extracted from poultry meats.
(KDa)

| MAbs | chicken | turkey | duck |
| --- | --- | --- | --- |
| 6F7  | 120 | ND[a] | ND |
| 3E12 | 34; 30; 25; 24 | 30; 29; 23.5; 22 | 30 |
| 1A5  | 34; 30; 25; 24 | 30; 29; 23.5; 22 | 30 |
| 5D2  | 35; 30; 25; 23.5 | 29.5; 26; 24.5; 22 | ND |
| 6G8  | 35; 30; 25; 23.5 | 29.5; 26; 24.5; 22 | ND |

[a]not detectable

EXAMPLE 2

Materials and Methods

Extraction of Cooked Meat Soluble Proteins

Muscle samples were purchased from a local supermarket (lamb, turkey and duck) or obtained from the Auburn University Meats Laboratory (pork, beef and chicken) and College of Veterinary Medicine (horse and deer), Auburn University.

Extraction of soluble proteins was performed as follows. Samples from each species was blended separately. Thirty grams of trimmed, lean meat from each species were cut into small pieces and blended separately by blender (Virtis Model 45, Gardiner, N.Y.) for 1 minute. Three fold (w/v) of deionized water was added to each sample. These homogenates were cooked and boiled at 100° C. for 15 minutes. The soluble proteins were extracted by gentle agitation of these homogenates for 2 hours at 4° C. then centrifuged at 14,300×g at 4° C. for 30 minutes (Beckman J-21C, Palo Alto, Calif.). Supernatants were filtered through Whatman No 1 filter paper (Maidstone, Kent, England) and stored at −80° C.

The protein concentration of the extracts was determined by Bio-Rad protein assay kit 1i according to manufacturer's protocol(Bio-Rad, Hercules, Calif.). The assay was based on the method of Bradford (1976) *Anal. Biochem.* 72:248–254. Bovine serum albumin was used as standard in this assay.

Mice Immunization

The antigen used for immunization was protein extract of cooked pork described previously. Four 10-week-old female BALB/c mice (PRN 9612-R-0597) were immunized intraperitoneally or subcutaneously with approximately 0.4 ml of an emulsion containing equal volumes of antigen (50 μg of cooked pork soluble protein) and complete Freund's adjuvant (Sigma, St. Louis, Mo.). Three weeks later, mice were boosted with the same dose of antigen emulsified in incomplete Freund's adjuvant (Sigma). Sera were collected by tail vein bleeding one week after the booster. The sera were used to test specific antibody production by indirect ELISA. Four days before fusion, a final booster was done by injecting intraperitoneally with 50 μg of antigen suspended in 200 μl 0.01 M pH 7.2 phosphate buffered saline (PBS).

Production of Monoclonal Antibodies

Four days after the final booster, the injected mouse was sacrificed by cervical dislocation. The spleen was removed aseptically and cells were teased and flushed from spleen by a large blunt forceps and 10 ml of wash media (RPMI-1640 supplemented with 1% oxaloacetate, pyruvate, and insulin (OPI), 1% glutamine, 1% penicillin and streptomycin (p/s)) (Sigma) in a 10 ml syringe. The spleen cells were fused with murine myeloma cell line P3×63, Ag8.653, ATCC CRL 1580, in a 2:1 ratio by using 50% polyethylene glycol (PEG) 4000 (Sigma) as the fusion agent. One ml of 50% PEG was gently added to the cells dropwise. After standing for 1 minute, 30 ml of wash media was added to cells dropwise. The fused cells were resuspended in Hypoxanthine-aminopterin-thymidine (HAT) selective growth medium (RPMI-1640 supplemented with 15% fetal bovine serum (FBS), 1% OPI, 1% glutamine, 1%p/s and 1% HAT) (Sigma) and seeded in 96-well tissue culture plates set with mouse thymocyte feeder cells. The hybridoma cells were incubated at 37° C. with 5% $CO_2$ (Napco $CO_2$ incubator model 6300, Tualatin, Oreg.).

Hybridoma cell growth was apparent 10 to 14 days after fusion. When the culture fluids became acidic, the hybridoma supernatants were screened by indirect ELISA against cooked pork antigen. Hybridoma supernatants from the positive wells were also tested against protein extracts from cooked beef, lamb, deer, horse, chicken, turkey and duck.

Antibody-producing hybridoma cells of interest were selected and recloned two times by limiting dilution (Campbell, 1991). Cells were diluted with complete growth media (RPMI-1640 supplemented with 15% FBS, 1% OPI, 1% glutamine and 1% p/s) to give a concentration of 0.5 cell or 1 cell per well. Two hundred μl of each dilution were plated into each well of 96-well plates seeded with mouse thymocyte feeder cells. The recloned hybridoma cells were screened using the method describe previously. The antibody-producing hybridoma cells of interest were expanded to 48-well, 24-well, 12-well plate, small and large petri dish, sequentially. Finally, they were frozen and stored in liquid nitrogen (Procedure B, page 32).

Production of Ascites Fluid

For producing large amount of MAbs, normal adult BALB/c mice were primed intraperitoneally with 0.5 ml of pristane. One week later, the mice were inoculated intraperitoneally with $1\times10^7$ hybridoma cells in 500 μl of PBS. Approximately 10 to 14 days after inoculation, ascites fluid was collected daily for a week. Ascites fluid containing MAbs was centrifuged at 2,000×μg for 5 minutes to remove cells then stored in a sterile centrifuge tube at 4° C.

ELISA

Indirect non-competitive ELISA was used in this study. Two μg of pork antigen or protein extracts from eight cooked meat species in 100 μl of carbonate buffer (0.06 M pH 9.6) was coated to each well of 96-well round-bottomed vinyl microtiter plate (Costar, Cambridge, Mass.) and incubated for 1 h at 37° C. or at 4° C. overnight. After washing three times with 0.01 M phosphate buffered saline, pH 7.2, containing 0.5% Tween-20 (PBST) using an microplate washer (Bio-Rad model 1250), 100 μl of 1% bovine serum albumin (Sigma) in PBS were added to each well to block nonspecific binding sites and the plate was incubated for 1 h at 37° C. After washing three times with PBST, 100 μl of hybridoma cell supernatant were then added to each well and incubated for 1 h at 37° C. After another three washes with PBST, 100 μl of diluted (1:3000 in PBS) horseradish peroxidase conjugated goat anti-mouse IgG (H+L) (Bio-Rad) were added. Following incubation for 1 h at 37° C., the plate was rinsed three times with PBST, and 100 μl of substrate solution containing 2,2'-azino-di-[3-ethyl-bezthiazoline-6-sulfonic acid] and hydrogen peroxide (Bio-Rad) was added to each well. After 10 min incubation at 37° C., the reaction was stopped by adding 50 μl of 10% oxalic acid and the absorbance was measured at 415 nm with a microplate reader (Bio-Rad model 450).

Isotyping of MAb

The isotype of MAb was determined by a mouse monoclonal antibody isotyping kit according to manufacture's protocol (Sigma).

Protein Extract Concentrating

Protein extracts of cooked meats were concentrated by ultrafiltration (Model 8050, Amicon, Bervely, Mass.) using a YM-10 membrane (Amicon). Nitrogen was applied to the system at 2114 $g/cm^2$ to facilitate the filtration process.

SDS-PAGE and Western Immunoblotting

Sodium dodecyl sulfate-polyacrylamide gel electrophoresis (SDS-PAGE) was performed to resolve the protein extracts of different cooked meat species. Western blot was then carried out to transfer proteins from gel to nitrocellulose membrane and to determine the molecular weights of proteins which reacted with developed MAbs. A Mini-Protean II electrophoresis unit (Bio-Rad) was used to perform SDS-PAGE. Proteins were separated on 4% acrylamide stacking gel (pH 6.8) and a 12% acrylamide separating gel (pH 8.8). The concentrated protein extracts of different cooked meat species were diluted with equal volume-of sample buffer containing 2% (wt/vol) SDS, 5% (vol/vol) β-mercaptoethanol, 60 mM Tris hydrochloride (pH 6.8), 25% (vol/vol) glycerol and 0.0001% (wt/vol) bromophenol blue (Laemmli (1970) *Nature* 227:680–685), boiled for 2 minutes, cooled and applied to the gel at approximately 10 μg per well. A constant voltage of 200 V was applied on the gel for 45 minutes by using a power supply (Model power pac 3000, Bio-Rad). After electrophoresis, the resolved protein bands were transferred to nitrocellulose membranes (Bio-Rad) by the method of Towbin et al. (1979) *Proc. Natl. Acad. Sci. USA* 76:4350–4354, using a electroblotting apparatus (Bio-Rad). Blotting was performed at 100 V for 1 hour in blotting buffer containing 20 mM Tris, 250 mM glycine and 20% methanol. Upon completion of the electroblotting, the nitrocellulose membrane was soaked in 3% gelatin (Bio-Rad) in PBS for 30 minutes to block the unspecific binding sites. The membrane was incubated with hybridoma supernatant in antibody buffer (1% gelatin in TBST) overnight at room temperature after two washes in Tris-buffered saline with Tween (TBST) (TBS, pH 7.5, containing 0.05% Tween-20). Following two washes in TBST to remove the excess MAb, the membrane was incubated with goat anti-mouse IgG alkaline phosphatase conjugate diluted in antibody buffer (1:3000) for 1 hr at room temperature. After washing with TBST two times, and an additional wash with TBS, the membrane was incubated with 5-bromo-4-chloro-3-indolyl phosphate/p-nitroblue tetrazolium chloride (BCIP/NBT) in alkaline phosphatase color development solution (0.1 M, pH 9.5 Tris buffer) (Bio-Rad). When dark purple bands which indicated the antibody binding site appeared on the membrane, the reaction was stopped by washing the membrane in distilled water. The prestained PAGE broad range standards including myosin (M. Wt. 205,000), β-galactosidase (M. Wt. 116,500), bovine serum albumin (M. Wt. 80,000), ovalbumin (M. Wt. 49,500), carbonic anhydrase (M. Wt. 32,500), soybean trypsin inhibitor (M. Wt. 27,500), lysozyme (M. Wt. 18,500) and aprotinin (M. Wt. 6,500) were used as molecular weight markers in Western immunoblotting.

Preparation of Adulteration Standards

The protein extract of cooked pork and/or beef was used as adulterant to cooked chicken. A different percentage (vol/vol) (0, 0.5, 1, 5, 10, 15, 20, 25, 30, 50, 75, 100%) of adulterating protein extract was mixed with pure protein extracts of cooked chicken, respectively. Protein concentration was calculated for each mixture according to the amount of protein in each pure protein extract.

Results

Figure 7:
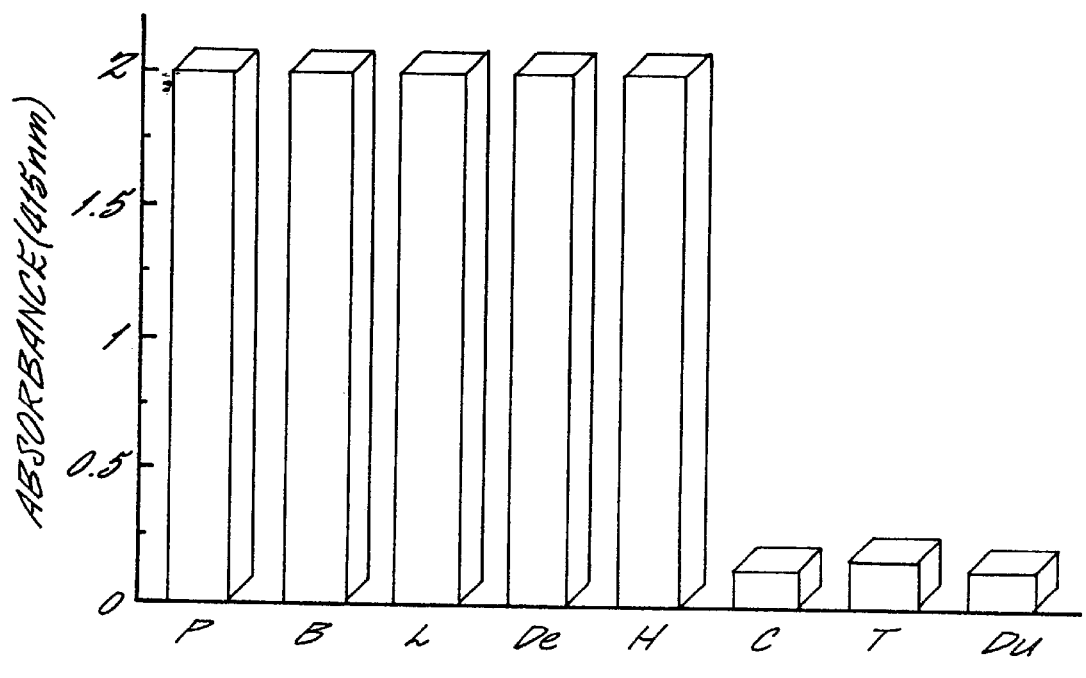
FIG. 7 The specificity of MAb 2F8 to cooked meat determined by indirect ELISA. Data shown are the means of three readings. P: pork; B: beef; L: iamb; De: deer; H: horse; C: chicken; T: turkey; Du: duck.

During the screening process, numerous hybridoma clones produced MAbs against the cooked pork antigen. After recloning and testing cross-reactivity to other species (beef, lamb, deer, horse, chicken, turkey and duck), only one stable hybridoma cell line, 2F8, which secreted IgG2b type of MAb, was chosen. Because IgM antibodies are generally harder to purify and store, they were avoided in this study by selecting only IgG MAbs using IgG τ-chain specific probes, i.e., enzyme conjugated goat anti-mouse IgG (H&L) was used as the secondary antibody in the ELISA screening procedures. MAb 2F8 reacted with all five cooked mammalian muscle proteins (pork, beef, lamb, deer and horse) but showed no cross-reactivity to poultry muscle proteins (chicken, turkey and duck) or raw lamb and deer proteins (FIG. 7). A slight increase of ELISA background absorbance (<0.2) was observed in raw pork, beef and horse. Results suggested that proteins reacted with MAb 2F8 might be heat-denatured or heat degraded soluble proteins. This can be explained by the fact that after the heat treatment, the proteins unfolded and exposed epitopes which could be recognized by MAb 2F8. Native proteins, however, did not react to this MAb.

The titers of the supernatant and ascites fluid of hybridoma cell line 2F8 against cooked proteins of each species were also determined by indirect ELISA (Table 4). The titer was represented as the highest reciprocal dilution fold that still gave an absorbance higher than 0.1 MAb 2F8 showed a higher reactivity to pork, beef and horse than lamb and deer. The reactivities to cooked pork, beef and horse were similar, while the reactions to cooked lamb and deer were slightly weaker. Both the supernatant and ascited fluid showed high titers to the five cooked mammalian muscle proteins.

A pure immunogen is not necessary for developing a desirable MAb and a MAb is not necessarily monospecific. In this study, a partially purified pork protein extract was used as immunogen because antiporcine antisera usually show strong reactivity to pork proteins as well as other mammalian proteins before eliminating the cross-reactive antibodies by affinity columns (unpublished observation). MAb 2F8 was purposefully induced and selected to react with common motifs in the proteins of five taxonologically related mammalian species.

Figure 8:
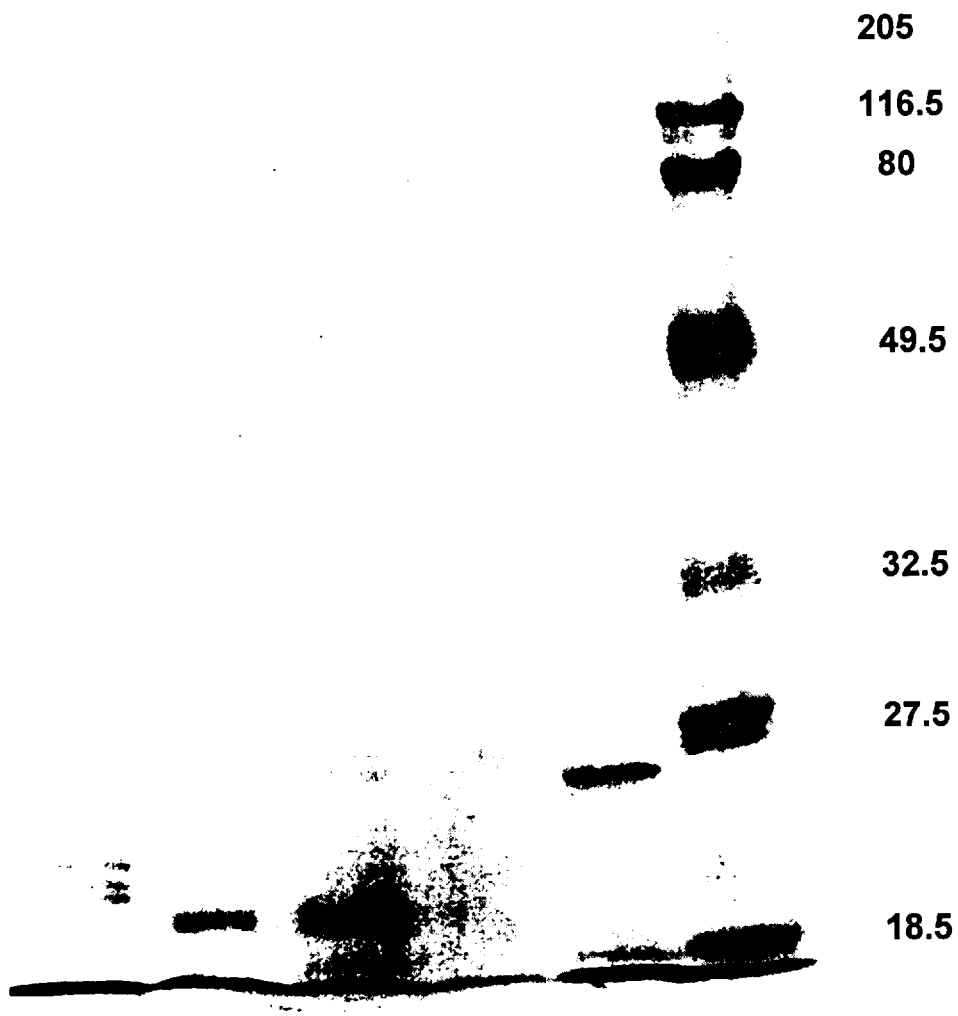
FIG. 8 Immunoblots of proteins extracted from five cooked mammalian meats separated on 12% (w/v) SDS-PAGE reacted with MAb 2F8. Lanes; 1=pork, 2=beef, 3=lamb, 4=deer, 5=horse, 6=Molecular weight standard.

Although MAb 2F8 could react to all five cooked mammalian muscle proteins, the components it reacted with were different among species. (FIG. 8). From the result of Western blotting, we found that the protein extracts of all five mammalian meats showed two or more protein bands reacting with MAb 2F8 (FIG. 2) indicating that cooked meat proteins may be multivalent antigens. It could also be the identical sequential determinants carried by degradation products of different sizes. The molecular size of these immunogenic components were small, ranging from 6.5 to 26.5 kDa, suggesting that they were either small proteins or heat degraded protein subunits or peptides. The dye front protein band (6.5 kDa) was present in all five species. Because pork muscle proteins were used as the immunogen to develop the MAbs, pork had the most immunogenic components (6 bands) that reacted with MAb 2F8. Beef showed 2 bands, horse 3, lamb 4, and deer had 2 bands. The number of immunogenic components in each species, however, did not correspond to the reactivity of MAb 2F8 to each species from ELISA responses. Epitopes available for antibody binding depend on antigen concentration and conformation. Some epitopes may be embedded inside of the antigen but were exposed after SDS-denaturation and thus be recognized by MAb 2F8.

The MAb 2F8 was further used to detect and quantify the amount of five mammalian animal meats in cooked chicken meat mixtures by ELISA. As shown in FIG. 3, the absorbance values increased proportionally with the increase of the amount of target species until a 15% substitution of pork, beef or horse was achieved in chicken. Because of the strong reactivity of MAb 2F8, the absorbances for the substitution higher than 15% were overscaled. At least 0.5% of adulteration of pork, beef, horse, and lamb could be detected using this MAb in indirect ELISA. For the substitution with lamb, the absorbance was proportional to the concentration of lamb meat in the range 0–50%. The substitution with deer showed the lowest reactivity with 5% and above of deer substitution being detected. The absorbance was not overscaled until it reached 75% of substitution with deer in chicken. The detection limit of this assay was defined as two standard deviation apart from the mean reading of the meat matrix containing no mammalian meat. The assay showed a good discrimination between chicken containing no mammalian meats and those containing a low amount of these meats.

Martin et al. (1991) *Meat Sci.* 30:23–31, detected 1–100% chicken meat in the mixture of raw beef and pork by a MAb-based sandwich ELISA. By using polyclonal antibodies-based ELISA, beef containing 0.5% of pork and beef products with 1% of the lean pork could be differentiated visually (Jones and Patterson (1985) *Meat Sci.* 15:1–13). Stevenson et al. (1994) Food Agric. Immunol. 6:297–304, also reported the detection of chicken in beef at 1% level by indirect ELISA with polyclonal antibodies as capture reagent. All of the antibodies mentioned above were developed to identify one species at a time. Recently, Billett et al. (1996) *J. Sci. Food Agric.* 70:396404, developed MAb to detect a group of poultry meats (chicken, turkey, pheasant and duck) at the 100 g per kg (10%) mixed meats level. MAb 2F8, however, has potential to be used for detection and quantification of mammalian meats in cooked poultry meats at low levels of adulteration (0.5%) and over a wide range of adulteration levels. Research in optimizing ELISA method employing other formats such as, double sandwich ELISA, competitive ELISA and using streptoavidin-biotin amplification system, is ongoing in our laboratory to further increase the detection limit and achieve quantitative measurements in various types of meat product.

When cooked chicken meat was adulterated with a mixture of beef and pork, the ELISA absorbance reflected the total amount of the two adulterating species (Table 5). The mean absorbance readings ranged 0.802 to 1.149 and 1.644 to >2 for a total of 5% and 10% level of substitution, respectively. The absorbance was overscaled for all combinations of 15% substitution. Results suggested that although differentiating species among the five mammalian meats was not possible, a total amount of mammalian meat adulterants could be semiquantitatively determined using MAb 2F8.

The consumption of poultry has been increasing due to health concerns of less saturated fat and a lower price in comparison to mammalian meats. Hsieh et al. (1995) *J. Food Prot.* 58:555–559, reported that beef or sheep meats were found as contaminating species in ground turkey on retail markets. The reasons for substituting cheaper meat such as poultry with more expensive meat like beef and sheep include the use of the unmarketable trimmings from expensive meats and improper cleaning of the grinder between each change of meat species for grinding. The widespread species adulteration in retail markets may be attributed to the inadequate meat inspection and the lack of a suitable and affordable analytical method. Using ELISA with MAb 2F8, the presence of any of the five mammalian meat adulterants in a cooked poultry could be detected with a single test visually or semiquantitatively. The developed MAb should be useful in an initial rapid screening test for a large number of samples in a laboratory and it can be made into a field test kit for meat processors and inspectors to be used on site. Money and time could be saved, reserving resources so even more samples could be tested and more retail stores inspected. Furthermore, this MAb can be used for not only cooked but raw meat species identification. For testing raw meats, only an additional heat treatment (100° C., 15 min) is required during sample preparation.

TABLE 4-continued

Titration of monoclonal antibodies against cooked five land animal meats by indirect ELISA[a]
MAb 2F8

| Supernatant | Ascites Fluid |
|---|---|
| lamb4096 | $3.3 \times 10^6$ |
| deer4096 | $3.3 \times 10^6$ |
| horse8192 | $6.6 \times 10^6$ |
| chicken4 | 1600 |
| turkey8 | 1600 |
| duck4 | 1600 |

[a]Titers were represented as the highest dilution of supernatants that had absorbance above 0.1.
[b]Means of triple readings.

PROCEDURE A.
RETRIEVE MYELOMA CELLS FROM LIQUID NITROGEN 1. retrieve myeloma cells from liquid nitrogen
2. put the vial into a 37–39° C. water bath to thaw the cells
3. add 9 ml of growth media (RPMI-1640, 10% FBS, 1% p/s) drop by drop to resuspend the cells
4. centrifuge at 1,700 rpm for 5 min
5. resuspend cell pallet in 5 ml of growth media
6. perform the cell count
7. centrifuge at 1,700 rpm for 5 min
8. resuspend the cells in 5 ml of growth media
9. transfer the cells to the petri dish

PROCEDURE B.
PROCEDURE OF FREEZING HYBRIDOMA CELLS

1. Scrape cells from the petri dish
2. centrifuge at 1700 rpm for five minutes to get cell pallet
3. resuspend cell pallet with 500 μl of CGM
4. Add 500 μl of freeze media containing six parts of FBS, two parts of CGM and two parts of dimethyl sulfoxide (DMSO) drop by drop
5. Cell suspension was transferred to a cryogenic vial and stored in liquid nitrogen.

TABLE 5

Indirect ELISA response expressed as absorbance (A) at 415 nm for cooked chicken substituted by various combinations of cooked pork (P) and beef (B) at total concentrations of 5%, 10%, and 15% by weight.

| 5% | $A_{415a}$ | 10% | $A_{415}$ | 15% | $A_{415}$ |
|---|---|---|---|---|---|
| 1% P + 4% B | $0.840 \pm 0.031$[a] | 1% P + 9% B | $1.671 \pm 0.097$ | 2% P + 13% B | >2 |
| 2% P + 3% B | $0.873 \pm 0.009$ | 3% P + 7% B | $1.781 \pm 0.027$ | 5% P + 10% B | >2 |
| 3% P + 2% B | $0.802 \pm 0.003$ | 5% P + 5% B | $1.604 \pm 0.025$ | 8% P + 7% B | >2 |
| 4% P + 1% B | $1.149 \pm 0.032$ | 8% P + 2% B | >2 | 10% P + 5% B | >2 |
| 5% P | $1.014 \pm 0.015$ | 10% P | >2 | 15% P | >2 |
| 5% B | $1.008 \pm 0.011$ | 10% B | $1.775 \pm 0.021$ | 15% B | >2 |

[a]Values represented are means ± SD (n = 6).

TABLE 4

Titration of monoclonal antibodies against cooked five land animal meats by indirect ELISA[a]
MAb 2F8

| Supernatant | Ascites Fluid |
|---|---|
| pork8192[b] | $6.6 \times 10^6$ |
| beef8192 | $6.6 \times 10^6$ |

EXAMPLE 3

Methods

Sample Preparation

Beef was trimmed off external fat and connective tissue and ground twice using a hand grinder. Samples were stored in a freezer at −20° C. until use. After thawing, eight grams of ground beef were packed into the bottom section of 22 mm×150 mm glass tubes. Temperature was monitored by inserting a stainless steel probe into the geometric center of the sample. The glass tubes with sample were placed in a temperature-controlled circulated water bath maintained at desired target temperatures. When internal temperature of the sample reached the target temperature (0–100° C.), tubes were removed and immediately cooled in an ice-water bath.

Cooked beef samples were homogenized in 1:3 volumes (w/vol) of 0.85% NaCl. The slurry was centrifuged at 5,000×g for 15 min at 4° C. The supernatant was filtered through a Whatman no. 1 filter paper. Soluble protein content of the filtrate was determined by dye binding assay (Bio-Rad) using bovine serum albumin as standard.

ELISA Procedure

Optimization of the ELISA procedures was achieved by cross titration of antigen (meat extract) and antibody. The indirect ELISA was performed by coating polyvinyl microtiter wells with 100 ul of 0.1 M carbonate buffer (pH 9.6) containing 0.25 ug of soluble proteins from the extract. Plates was incubated at 37° C. for 1 hr and placed in a refrigerator at 4° C. overnight. Wells were washed three times with PBST and remaining binding sites were blocked by adding 150 ul of 1% BSA-PBS and incubating at 37° C. for 1 hr. MAb 2F8 diluted 1:6400 in PBS was added to wells (100ul per well); plate was incubated for 1 hour at 37° C. After washing with PBST, IgG peroxidase conjugate diluted (1:2500) in PBS was added to each well. Plate was incubated for 1 hr at 37° C. and washed five times, and bound peroxidase was determined with ABTS substrate. Absorbance was read at 405nm using a Microtiter plate reader (Bio-Rad).

SDS-PAGE and Western Blotting

SDS-PAGE was used to determine protein composition of the meat extracts. Soluble proteins were separated on a 12% acrylamide gel using a Mini-Protein II electrophoresis unit (Bio-Rad). The resolved protein bands were transferred electrophoretically from the SDS-PAGE gel to a nitrocellulose membrane. The reaction of proteins with MAb 2F8 was detected by goat anti-mouse IgG alkaline phosphatase conjugate followed adding of the enzyme substrate.

Results and Discussions

Figure 9:
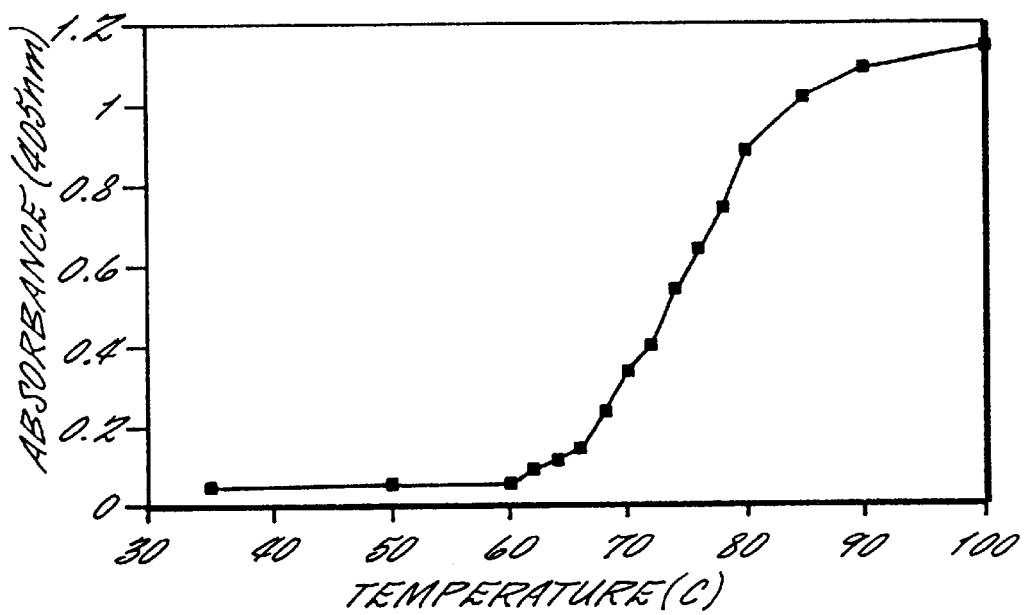
FIG. 9 Indirect ELISA responses of MAb 2F8 to protein extracts from beef cooked to different end point temperature (EPT). (Values are the mean of eight replications).
Figure 10:
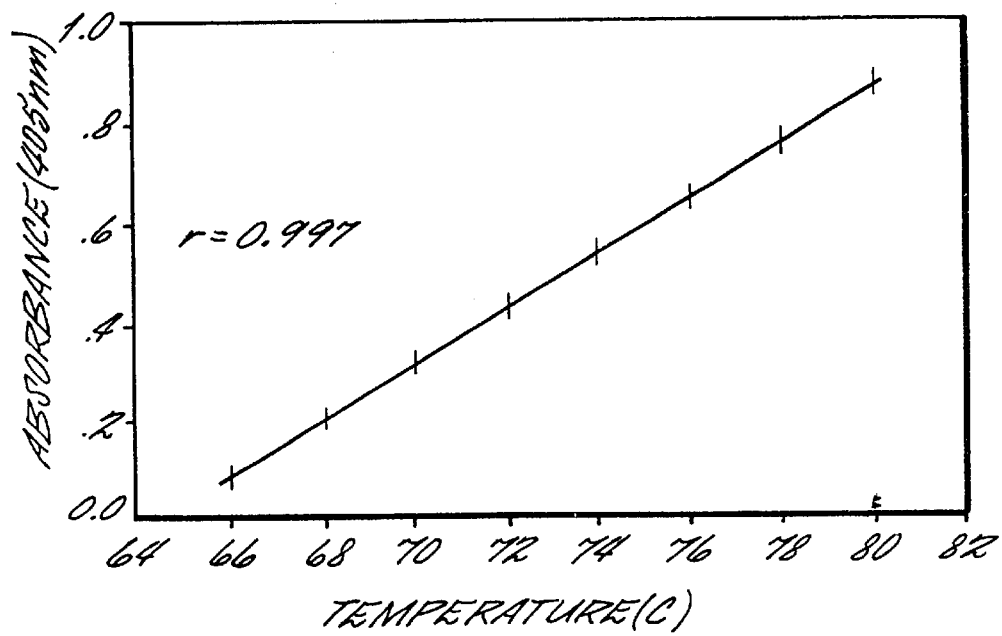
FIG. 10 Linear regression of indirect ELISA response and EPT of cooked beef using MAb 2F8. (Correlation coefficient was determined by eight replicate values).

ELISA response to the beef extract showed a temperature-dependent reactivity (FIG. 9). Binding of MAb2F8 to soluble proteins of beef extract was extremely low when samples were cooked to end-point temperatures of 60° C. or below. ELISA responses slightly increased as cooking temperature increased from 60° C. to 66° C.; increased rapidly and constantly from 66° C. to 80° C. Temperature required for denaturing the majority of beef soluble proteins has been observed within the range of 60° C. to 80° C. Meat extracts from different cooking temperatures can be differentiated at least at 2° C. intervals ranging from 66° C. to 80° C. (P<0.05). A linear increase of the reactivity, with a correlation coefficient of 0.997, was also observed as increase of the end-point temperature from 66° C. to 80° C. (FIG. 10). These results suggest that determination of end-point temperature of cooked beef can be achieved within this range using MAb 2F8.

Figure 11:
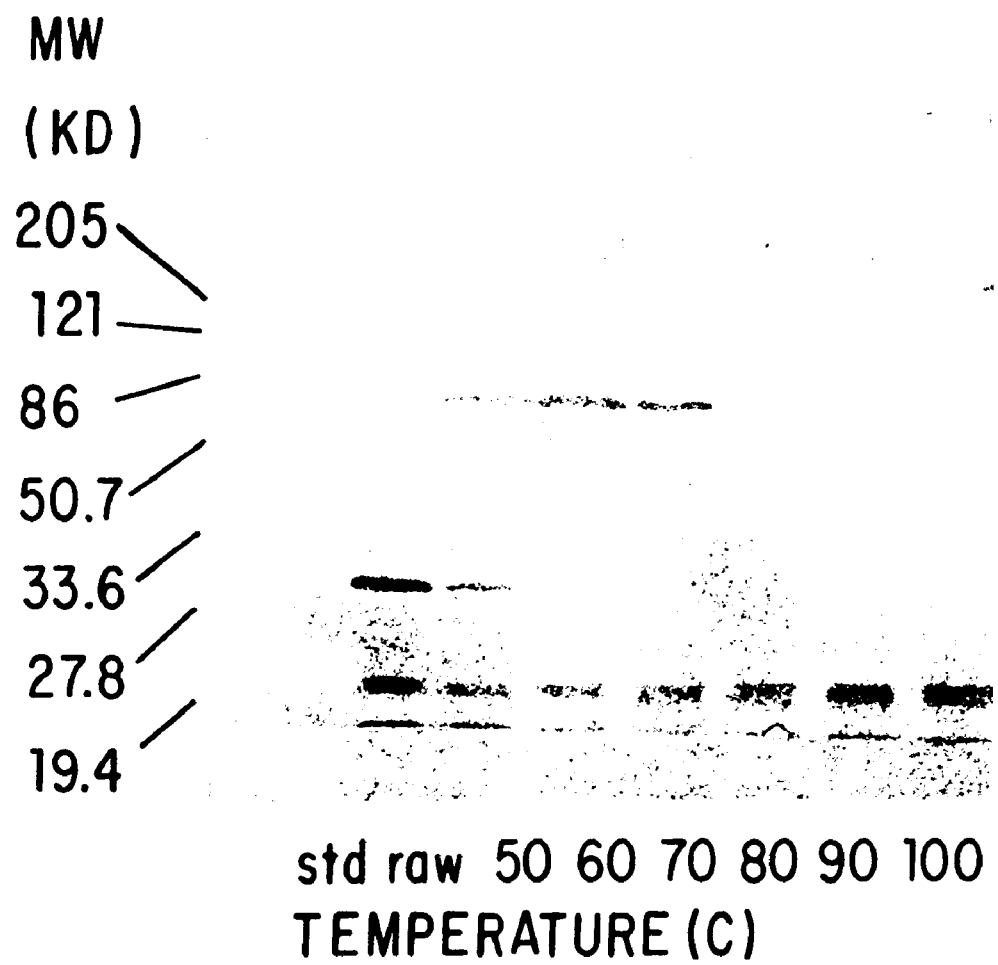
FIG. 11 Western blot of muscle extracts from beef cooked to different EPT. MAb 2F8 was used as probing agent.

Soluble protein patterns at different temperatures were obtained by SDS-PAGE of the cooked beef extracts (not shown). Solubility of muscle proteins decreased rapidly when beef was heated between 50° C. and 70° C. and remained fairly constant above 80° C. The binding of MAb 2F8 to the antigen was further examined by Western Blot (FIG. 11). MAb bound to proteins with molecular weight of 21 KD and others with molecular weight smaller than 19.4 KD in all cases; in addition, several soluble proteins with large molecular weight could also be detected by the MAb when beef was heated below 70° C. or when the raw meat extract was denatured by SDS treatment. It appeared that this MAb recognized a group of soluble proteins which contribute a common epitope on their surface after denaturation. As the heating temperature increased, most of the proteins which were present in the raw meat extract became insoluble; only the proteins retained in the cooked meat extract were detected by the MAb. Because of the same amount of proteins was applied in our ELISA procedures, the increase of the reactivity was attributed to the increase of thermally induced changes of the proteins as detected by the MAb. It may be that heat treatment induces the structural changes of the protein molecules and exposes the epitope region which is absent or rare on the native molecules. The changes may be conformational or alternatively may to due to the fragmentation of native proteins. Proteins with varied sensitivity to heat treatment expose these epitope at different temperature range; this can be a possible reason for the observed temperature-dependent responses in our ELISA procedures.

These finding leads us to propose the use of denatured soluble proteins as an indication of end-point temperature of cooked meat products. Most of the currently developed methods were based on detection of single protein marker or enzyme activity. The distribution of the protein or enzyme, however, varies depend on the different portion of muscle tissue. Detection of proteins as a group in terms of their immunoreactivity after denaturation appears to be less influenced by these factors.

Undercooked meat products are responsible for numerous foodborne outbreaks. Valid methods for evaluating the adequacy of heat processing in cooked meat will significantly reduce this risk of the consumer. Most currently developed methods were based on the decrease of protein solubility or residual enzyme activity as an indication of EPT. They have inherent limitations including the relatively low sensitivity, narrow temperature range and variation among different muscle tissues. USDA-FSIS suggested that new approaches should be explored, such as determining the increases of some chemical compounds as EPT increases (Ang, et al., 1994).

As is evident in our study, using MAb as a probe to detect the heat induced conformational changes of the soluble muscle is feasible. The most attractive features of our proposed approach are: (1) Measurements based on the protein denaturation are positively related to heat treatment; (2) High sensitivity of ELISA provides accurate and rapid screening of a large number of samples; (3) Monitoring the denaturation of a group of proteins has less variation than a single protein marker, and (4) Wide temperature range application is possible. The developed MAb based ELISA may be commercialized as test kit for use by the food industry, food service operations and regulatory agencies.

EXAMPLE 4

Monoclonal Antibodies for Detection of Pork

Methods for identification of raw meat based on ELISA have been well established (Whittaker, R. G., Spencer, T. L., and Copland, J. W. (1983) *J. Sci. Food Agric.*, 34:1143–1148; Griffiths, N. M., and Billington, M. J. (1984) *J. Sci. Food Agric.* 35:909–914; Patterson, R. M., Whittaker, R. G., and Spencer, T. L. (1984) *J. Sci. Food Agric.* 35:1018–1023; Jones, S. J., and Patterson, R. L. S. (1986) *J. Sci. Food Agric.* 37:767–775; Martin, R., Azcona, J. I., Casas, C., Hernandez, P. E., and Sanz, B. (1988) *J. Food Prot.* 51:790–794; and, Ayob, M. K., Ragab, A. A., Allen, H. C., Farag, R. S., and Smith, C. J. (1989) *J. Sci. Food Agric.* 49:103–116). Detection of species adulteration in cooked meats appears to be more complicated than in the raw meats because heat induces denaturation of most immunogenic proteins. Therefore, the antigens for cooked meat identification should be able to withstand cooking or can be renatured after heating.

Hybridoma techniques, developed by Kohler and Milstein enable continuous production of MAbs with defined specificity (Kohler, G., and Milstein, C. (1975) *Nature* 256:495–497). MAbs have been applied to ELISA for raw meat identification (Martin, R., Wardale, R. J., Jones, S. J., Hernandez, P. E., and Patterson, R. L. S. (1991) *Meat Sci.* 30:23–31; Garcia, T., Martin, R., Morales, P., Haza, A. I., Anguita, G., Gonzalez, I., Sanz, B., and Hernandez, P. E. (1994) *J. Sci. Food Agric.* 66:411–415; Morales, P., Garcia, T., Gonzalez, I., Martin, R., Sanz, B., and Hernandez, P. E. (1994) *J. Food Prot.* 57:146–149; Billett, E. E., Bevan, R., Sanlon, B., Pickering, K., and Gibbons, B. (1996) *J. Sci. Food Agric.* 70:396–404). However, MAbs are not available for detection of species adulteration in cooked meat products. The production of species-specific MAbs to the thermal-stable muscle proteins (TSMPs) provide an unlimited supply of uniform reagents capable for both raw and cooked meat identification. Therefore, the present invention provides (1) MAbs specific to pork TSMPs, (2) porcine-specific MAbs and their correspondent antigens, (3) a MAb-based ELISA for detection of pork in raw and cooked meat products.

Materials and Methods

Antigen Preparation

TSMPs from pork were prepared by modifying the method described by Milgrom and Witebsky (1962) *Immunology* 5:46–66. Briefly, after removing fat and connective tissue, skeletal muscle tissue (100 g) was homogenized in 0.15 M CaCl (1:2 w/v) using an Brinkmann Polytron Homogenizer (Model PT 10/35, Brinkmann Instruments Co., Westbury, N.Y.). The slurry was further sonicated (50 W, 20 KHz, 5 min.) with a Model 4710 Ultrasonic Processor (Cole-Parmer Instrument Co., Vernon Hills, Ill.), heated in boiling water for 20 min, and centrifuged at 2,000 g for 30 min. The supernatant was autoclaved at 121° C. for 30 min, centrifuged at 5,000 g for 30 min and filtered through Whatman No. 1 filter paper. The precipitate was formed by adding 90% ethanol (1:3.74 vol/vol) and dried in a convection oven at 37° C.

Immunization

The dry material was dissolved in a small amount of saline solution; the protein concentration of the preparation was determined by a Protein Assay Kit (Bio-Rad, Hercules, Calif.) using bovine serum albumin (BSA) as a standard. Four female BALB/c mice (6–8 weeks) were injected either intraperitoneally or subcutaneously with 100 $\mu$g/mouse of the-TSMPs in 200 $\mu$l phosphate buffered saline (PBS, 0.15 M NaCl, 0.01 M sodium phosphate buffer, pH 7.2) emulsified with same volume of Freund's complete adjuvant. Four Boost injections prepared in the same manner using Freund's incomplete adjuvant were applied to each mouse at four week intervals. Test sera from mice were collected eight days after each boosting by tail bleeding; titer of the sera was determined by ELISA. The mouse showing the highest titer was injected intraperitoneally with 100 $\mu$g of TSMPs in PBS four days before fusion.

Monoclonal Antibody Production

The spleen cells from the immunized mouse were fused with myeloma cells for hybridoma production. The general procedures as described by Kohler and Milstein were followed with necessary modification to be performed in our laboratories (Kohler, G., and Milstein, C. (1975) *Nature*). Hybridomas were initially screened for reactivity to cooked pork extract by ELISA 10 to 14 days after fusion. The positive clones from the wells of original fusion plates were then transferred to larger wells and cultured for 2–3 more days; the culture supernatants were collected and tested against cooked meat extracts of other species. The hybridomas secreting antibodies react only with pork were selected and cloned twice by limiting dilution. MAbs were obtained in supernatants from propagated cell cultures and in ascitic fluid from mice inoculated with hybridoma cells. The isotype of MAbs were determined by a Mouse Monoclonal Antibody Isotyping Kit (Sigma Chemical Co., St. Louis, Mo.) following the manufacturer's instruction.

Epitope Comparison

A convenient ELISA method developed by Friguet et al. was adapted for comparison of relative binding sites of MAbs on the antigen (Friguet, B., Djavadi-Ohaniance, L., Pages, J., Bussard, A., and Goldberg, M. (1983) *J. Immun. Meth.* 60:351–358). Cooked meat extract from pork (0.5 $\mu$g protein/well) was coated onto the microtiter plate. The optimal dilution of each MAb was determined by checkerboard titrations to ensure sufficient antibody to saturate the antigenic sites of TSMPs. Same volume (50 $\mu$l each) of diluted MAbs to be compared was added to the well simultaneously; the amounts of bound antibody were quantitatively measured using procedures as described in the ELISA method.

Sample Preparation and Extraction

Meat samples of different origin (pork, beef, lamb, horse, deer, chicken, turkey, and duck) were obtained fresh and ground separately in our laboratory; ground meat samples were stored at −20° C. until use. Adulterated meat samples were prepared by mixing known amounts of pork (10, 20, 40, 80, 160, 320, 640 and 800 g/kg) in either beef or turkey. Cooked samples were prepared by packing 10 g of meat in 1.5×15 cm glass tubes and heating in boiling water for 20 min. Raw and cooked samples were extracted by adding 20 ml of saline solution to 10 g of meat and homogenizing in an Brinkmann Homogenizer. The slurry was set at 4° C. for 2 hr and filtered through a Whatman No. 1 filter paper. The protein concentration of the filtrate was determined using a Protein Assay Kit (Bio-Rad).

Indirect ELISA

Wells of microtiter plates (polyvinyl chloride plates, Costar, Cambridge, Mass.) were coated with 100 $\mu$l of meat extracts diluted in 0.06 M carbonate buffer (pH 9.6) at 37° C. for 1 hr; the protein content for coating was 2 $\mu$g/well for antisera titration, hybridomas screening, and meat sample analysis, and 0.5 $\mu$g/well for epitope comparison. Plates were washed three times with 200 $\mu$l of PBS containing 0.05% (vol/vol) Tween 20 (PBST) using a microplate washer (Bio-Rad, Model 1250) and incubated with 200 $\mu$l of blocking solution (1% BSA in PBS) at 37° C. for 1 hr to minimize nonspecific binding followed by another washing steps. Optimal dilutions for each MAbs were predetermined by checkerboard titrations. MAbs appropriately diluted in blocking solution (100 $\mu$l) were added to the well and the plate was incubated at room temperature for 1 hr. After washing the plate, 100 $\mu$l of horseradish peroxidase conjugated goat anti-mouse IgG (Bio-Rad) diluted 1:2500 in blocking solution was added to each well. The plate was incubated at room temperature for another 1 hr and washed six times before the addition of 100 $\mu$l of substrate solution (22 mg of 2,2'-azino-di-[3-ethyl-benothiazoline-6-sulfonic acid] and 15 $\mu$l of 30% hydrogen peroxide in 100 ml of 0.1 M phosphate-citrate buffer pH 4.0). Color development was processed at room temperature for 30 min and the enzyme reaction was stopped by adding 100 $\mu$l of 0.1 M citric acid to each well. Absorbance of each well was measured by a microplate reader (Bio-Rad, Model 450) at 415 nm.

Electrophoresis and Immunoblotting

Soluble proteins of meat extracts were separated by sodium dodecyl sulfate-polyacrylamide gel electrophoresis (SDS-PAGE) using a Mini-Protein II electrophoresis unit and a power supply Model 3000 (Bio-Rad) with stacking and separating gels of 4 and 12% acrylamide, respectively. Protein bands were stained with Coomassie Brilliant Blue R 250 and the apparent molecular weight of bands was calculated using a calibrating curve constructed from molecular weight standards. Soluble proteins of meat extracts were transferred electrophoretically (1 hr at 100V) from gel to nitrocellulose membrane using a Mini Trans-Blot unit (Bio-Rad) with 25 mM Tris, 192 mM glycerine, and 20% (vol/vol) methanol buffer (pH 8.3). Upon completion of the transferring, the membrane was washed with TBST (20 mM Tris, 500 mM NaCl, 0.05% Tween-20, pH 7.5), blocked with 20 ml of 3% gelatin in PBS for 1 hr, and incubated with 20 ml of ascitic fluid diluted 1:2000 in antibody buffer (1% gelatin in TBST) 2 hr at room temperature. The excess antibody was removed by washing with TBST, and the membrane was incubated with 20 ml of goat anti-mouse IgG alkaline phosphatase conjugate diluted 1:3000 in antibody buffer for 1 hr at room temperature. After washing, the membrane was incubated with 5-bromo4-chloro-3-indolyl phosphate/p-nitroblue tetrazolium chloride (BCIP/NBT) in 0.1 M Tris buffer, pH 9.5. The color development was observed between 10–20 minutes and straining was stopped by washing the membrane with distilled water.

Results and Discussion

Species Specificity of MAbs

Figure 12:
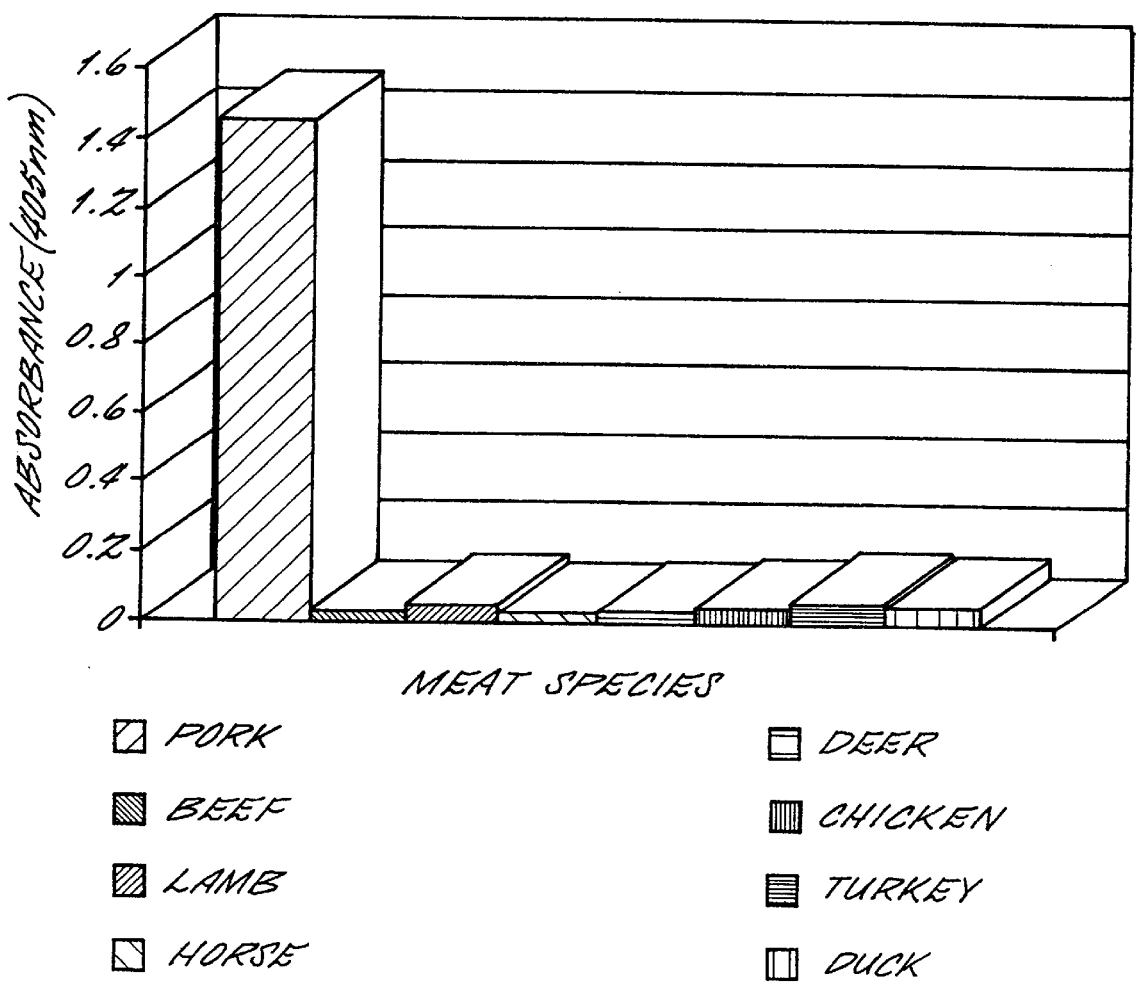
FIG. 12 The specificity of MAb 5H9 determined by indirect ELISA. Data shown are the means of three readings.

Four hybridoma cell lines, designated as 2E2, 5H8, 5H9 and 8A4, were selected after screening of supernatants from all wells of fusion plates. Isotype of MAbs secreted by these hybridomas was determined as IgG1 subclass. The quantity of MAbs was obtained in ascitic fluid for subsequent analysis; purification of MAb from ascitic fluid was not necessary because no significant nonspecific binding was observed and the ELISA performance was satisfactory when direct dilution of ascitic fluid was used. All MAbs reacted strongly with cooked pork extract and showed no cross-reaction with cooked meat extracts from beef, lamb, horse, deer, chicken, turkey and duck as determined by indirect ELISA (FIG. 12). A similar reaction pattern among the species also was observed for all MAbs when raw meat extracts were tested. The ability of the MAbs to detect both raw and cooked pork evidenced the heat resistance of the TSMPs which was present in raw meat and remained soluble and antigenic after cooking. During the checkerboard titrations, MAb 5H9 consistently showed higher maximum binding than the other three MAbs; this might be an indication of highest affinity of 5H9 among the four MAbs. Morales et al. produced a MAb specific to porcine muscle proteins for meat speciation (Morales, P., Garcia, T., Gonzalez, I., Martin, R., Sanz, B., and Hernandez, P. E. (1994) *J. Food Prot.* 57:146–149). Their method was able to detect the presence of pork in raw meat but not cooked products. The MAbs produced in this work is the first reported MAbs capable for identification of pork in both raw and cooked status.

Porcine-Specific TSMP

Figure 13:
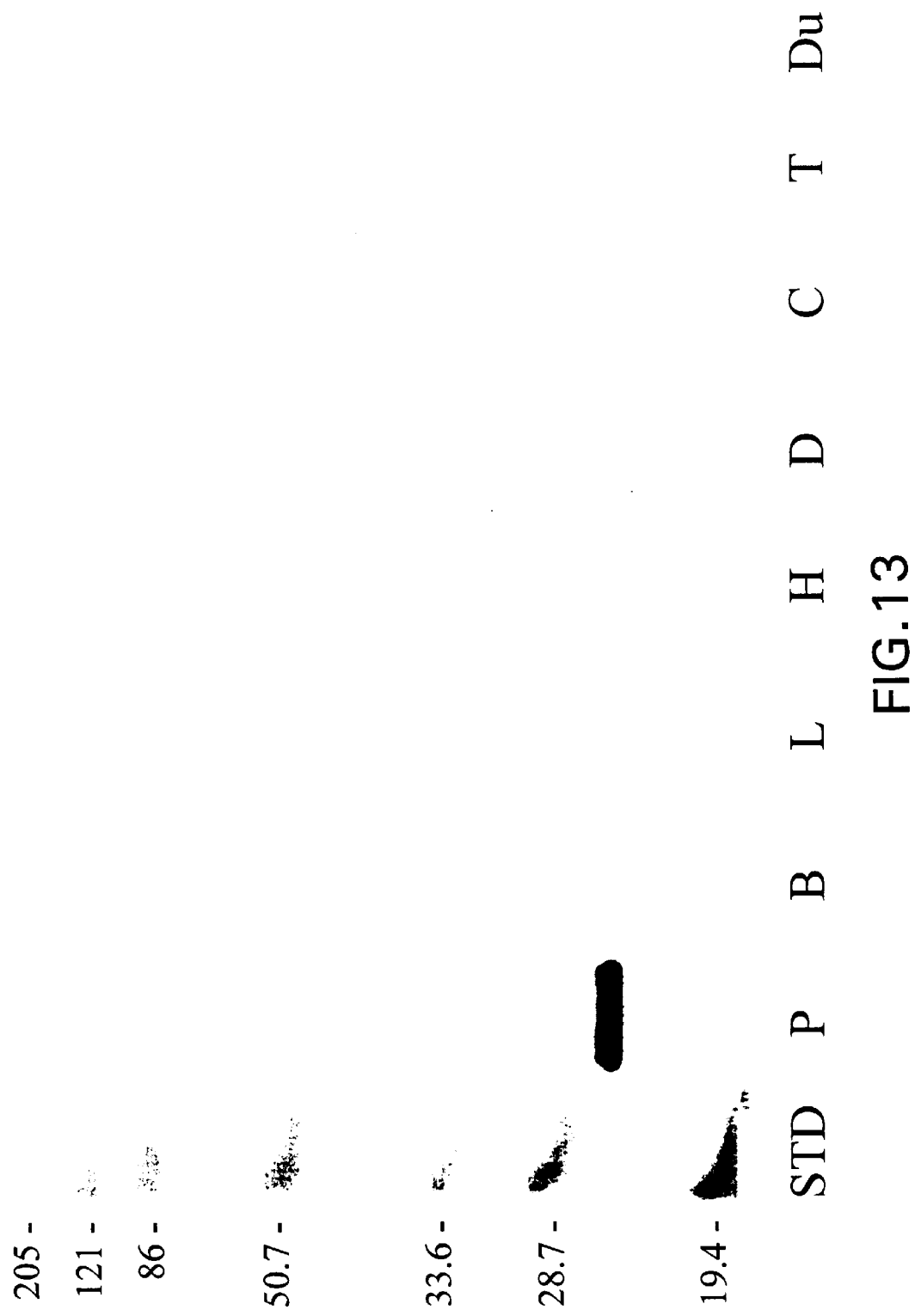
FIG. 13 A representative SDS-PAGE and Western blot showing the antigenic components in raw and cooked pork using MAb 5H9.

The ability of the MAbs to differentiate equivalent protein bands of pork from other species was observed when proteins were transferred from gel to nitrocellulose membrane and probed by MAbs to reveal the immunoreactive components in raw and cooked meat extracts. It is clear that all four MAbs reacted with proteins of pork origin but not with proteins from beef, lamb, horse, deer, chicken, turkey and duck. The results confirmed the porcine-specificity of MAbs observed previously by indirect ELISA. All of the MAbs showed the same reaction pattern on the immunoblot; three protein bands with an apparent molecular weight of 24, 22, and 20.5 kD in raw pork were recognized while only one protein band with a molecular weight of 24 kD was detected in cooked pork by all four MAbs. (FIG. 13) Failure to detect the two protein bands (22 and 20.5 kD) in cooked meat extract indicated the absence of these proteins which may become insoluble after heating. The 24 kD protein present in both raw and cooked pork extract was identified as porcine-specific TSMP. Several researchers have attempted to resolve the thermal-stable components of different meat species. Jones and Mortimer demonstrated that the thermal-stable proteins eluted in a low pH range (3.5–6.5) and characteristic pattern of thermal-stable protein from different species was not noticeably different using isoelectrofocusing (Jones, S. J., and Mortimer, R. H. (1985). Species identification of cooked meats by isoelectrofocusing: preliminary 25 studies to resolve heat-stable components isolated from adrenal and muscle tissue. In: *Biochemical Identification of Meat Species,* Patterson, R. L. S. (Ed.), p. 118–128. Elsevier Science Publishing, Inc., New York). Sherikar and coworkers reported that "troponin T", with a molecular weight of 36 kD, is the species-specific antigenic fraction of TSMPs (Sherikar, A. T., Karkare, U. D., Khot, J. B., Jayarao, B. M., and Bhilegaonkar, K. N. (1993) *Meat Sci.* 33:121–136). The present results did not agree on the identity of the species-specific TSMP, but did confirm the existence of this protein in muscle tissues. The production of MAb does not require a pure protein as an immunogen. MAbs to the species-specific components in partially purified muscle proteins can be selected by appropriate screening procedures (Garcia, T., Martin, R., Moreales, P., Haza, A. I., Anguita, G., Gonzalez, I., Sanz, B., and Hernandez, P. E. (1994) *J. Sci. Food Agric.* 66:411–415). In the present case, the occurrence of all four MAbs from different hybridoma cell lines coincidentally recognizing the same proteins indicated that the TSMP of 24 kD may be the only species-specific component present in the cooked pork extract.

Detection of Pork Adulteration

All four MAbs developed in this work exhibit several similar characteristics. MAb 5H9 with potentially higher affinity than others was chosen for the subsequent analysis. The optimal condition for ELISA was determined by checkerboard titrations. The highest sensitivity of assay was achieved using 2 µg/well of proteins from meat extracts and 1:102,400 dilution of ascitic fluid and 1:2,500 dilution of goat anti-mouse IgG horseradish peroxidase conjugate. The developed ELISA successfully detected adulteration of pork in raw and cooked meat mixtures. The detection limit of the assay, defined as two standard deviation apart from mean reading of the heterogenous meat matrix containing no pork, was 10 g/kg of pork in heterogenous meat mixtures which is adequate in determination of low level of adulteration of pork in meat products. The curvilinear relations of second-degree polynomial with high correlation coefficient ($r^2>0.995$) between pork contents and ELISA responses can serve as standard curves for quantifying pork in beef (7 6) and pork in turkey (Table 9) for both raw and cooked status.

TABLE 6

Detection of Pork in Beef by ELISA
Confidence limits for mean values of different percentages of pork in beef

| % pork in beef | mean OD* (405 nm) | Lower 99% | Upper 99% |
|---|---|---|---|
| 0 | .012 | .010 | .014 |
| 1 | .059 | .056 | .062 |
| 2 | .150 | .120 | .180 |
| 4 | .219 | .192 | .246 |
| 8 | .317 | .281 | .353 |

*mean of 5 replicates

TABLE 7

Detection of Pork in Turkey by ELISA
Confidence limits for mean values of different percentages of pork in turkey

| % pork in turkey | mean OD* (405 nm) | Lower 99% | Upper 99% |
|---|---|---|---|
| 0 | .004 | .003 | .005 |
| 1 | .024 | .020 | .028 |
| 2 | .041 | .036 | .046 |
| 4 | .141 | .125 | .157 |
| 8 | .282 | .247 | .317 |

*mean of 5 replicates

For raw meat speciation, serum proteins were used exclusively as antigens in developing immunoassays (Ayob, M. K., Ragab, A. A., Allen, H. C., Farag, R. S., and Smith, C. J. (1989) *J. Sci. Food Agric.* 49:103–116; Jones, S. J., and Patterson, R. L. S. (1986). A modified indirect ELISA procedure for raw meat speciation using crude anti-apecies antisera and stabilized immunoreagents. *J. Sci. Food Agric.* 37:767–775; Patterson, R. M., Whittaker, R. G., and Spencer, T. L. (1984) *J. Sci. Food Agric.* 35:1018–1023; Whittaker, R. G., Spencer, T. L., and Copland, J. W. (1983) *J. Sci. Food Agric.,* 34:1143–1148). However, the presence of serum protein is not necessarily correlated to the presence of the muscle tissue, the quantitative aspect of these assay is not reliable (Griffiths, N. M., and Billington, M. J. (1984) *J. Sci. Food Agric.* 35:909–914). Moreover, serum proteins are denatured under the cooking practice; the use of serum proteins for cooked meat identification is merely impossible. Assays based on detection of muscle proteins is more indicative for quantifying the presence of extraneous muscle tissue in meat mixtures. The use of insoluble myofibrillar proteins, such as desmin, as antigen increases the complexity of extraction procedures (Billett, E. E., Bevan, R., Sanlon, B., Pickering, K., and Gibbons, B. (1996) *J. Sci. Food Agric.* 70:396–404). The developed assay requires only a simple saline extraction which will reduce time and labor for sample extraction and facilitate analysis in large-scale screening tests.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for determining the end point temperature of a heat-processed meat sample, said method comprising the steps of:
   a) extracting proteins from a cooked meat sample to produce an extract; and
   b) contacting said extract with a monoclonal antibody having the binding specificity of 5D2 and capable of binding a heat-treated protein, wherein said heat-treated protein is a thermal-stable protein or a heat-degraded protein or a heat-denatured protein, and wherein the antibody exhibits an increase in reactivity with increased end-point temperature.

2. The method of claim 1, wherein said monoclonal antibody is 5D2.

3. The method of claim 1, wherein said sample consists of poultry meat.

4. A method for determining the end point temperature of a heat-processed meat sample, said method comprising the steps of:
   a) extracting proteins from a cooked meat sample to create an extract;
   b) using said extract to coat a solid surface;
   c) contacting said extract with a monoclonal antibody having the binding specificity of 5D2 and capable of binding a heat-treated protein so that at lea some of the monoclonal antibody binds to the sample on the plate;
   d) contacting said monoclonal antibody with a second antibody conjugated to a enzyme; and
   e) contacting said enzyme with a substrate so that an observable signal is generated.

5. The method of claim 4, wherein said monoclonal antibody is 5D2.

6. A monoclonal antibody capable of identifying poultry meat in a sample, wherein said antibody has the binding specificity of 5D2.

7. A kit comprising the monoclonal antibody of claim 6.

8. A method for detecting the presence of chicken or turkey meat in a heat-processed sample, said method comprising:
   a) contacting said sample with a monoclonal antibody having the binding specificity of 5D2; and
   b) determining whether said monoclonal antibody binds to said sample.

9. The antibody of claim 6, wherein said antibody is 5D2.

10. The method of claim 8, wherein said antibody is 5D2.

* * * * *

UNITED STATES PATENT AND TRADEMARK OFFICE
CERTIFICATE OF CORRECTION

PATENT NO. : 6,692,930 B2 Page 1 of 1
DATED : February 17, 2004
INVENTOR(S) : Hsieh It is certified that error appears in the above-identified patent and that said Letters Patent is hereby corrected as shown below:

Column 26,
Line 37, "lea" should read -- least --;
Line 40, "a" should read -- an --.

Signed and Sealed this

Fifteenth Day of June, 2004

JON W. DUDAS
*Acting Director of the United States Patent and Trademark Office*